United States Patent [19]
Yokoyama, deceased et al.

[11] Patent Number: 5,401,772
[45] Date of Patent: Mar. 28, 1995

[54] HETEROACETIC ACID DERIVATIVES

[75] Inventors: Naokata Yokoyama, deceased, late of Cliffside Park, by Rina Yokoyama, administrator; Gordon N. Walker, Morristown; Alan J. Main, Basking Ridge, all of N.J.

[73] Assignee: Ciba-Geigy Corporation, Ardsley, N.Y.

[21] Appl. No.: 154,203

[22] Filed: Nov. 18, 1993

Related U.S. Application Data

[63] Continuation-in-part of Ser. No. 918,544, Jul. 21, 1992, abandoned.

[51] Int. Cl.$^6$ .............................................. A61K 31/24
[52] U.S. Cl. ................................. 514/539; 514/616; 514/619; 514/563
[58] Field of Search ............... 514/534, 563, 616, 619, 514/539

[56] References Cited

U.S. PATENT DOCUMENTS

| | | | |
|---|---|---|---|
| 3,903,053 | 9/1975 | Iwata | 548/314.1 |
| 3,969,290 | 7/1976 | Kraft et al. | 260/2.5 |
| 4,036,837 | 7/1977 | Sellstedt et al. | 260/250 |
| 4,137,325 | 1/1979 | Sellstedt et al. | 424/311 |
| 4,154,961 | 5/1979 | Sellstedt et al. | 562/438 |
| 4,227,009 | 10/1980 | Koch et al. | 560/61 |
| 4,309,562 | 1/1982 | Takahashi et al. | 71/108 |
| 4,531,969 | 7/1985 | Nestler et al. | 71/108 |
| 4,656,183 | 4/1987 | Böger et al. | 213/64 |
| 4,976,773 | 12/1990 | Fukami et al. | 71/94 |

FOREIGN PATENT DOCUMENTS

| | | |
|---|---|---|
| 0138757 | 4/1985 | European Pat. Off. . |
| 2543179 | 4/1976 | Germany . |
| 0153325 | 2/1978 | Japan . |

OTHER PUBLICATIONS

J. Med. Chem., 1989, 32, pp. 320–336.
Nature, vol. 324, 425, (1986).
J. Med. Chem., 1984, 27, pp. 1587–1596.
The Journal of Biological Chemistry, vol. 251, No. 21, 1976, pp. 6489–6494.
Journal of Medicinal Chemistry, 1975, vol. 18, No. 9, pp. 926–933.
Atherosclerosis, 59, (1986) pp. 329–333.
Polish Journal of Chemistry, 57, 849 (1983).
Farm. Zh. (Kiev), 2, pp. 41–45 (1989).
Khim. Farm. Zh., 1(12), pp. 7–12 (1967).
Chem. Abstr. 89:24802b; 1978.

*Primary Examiner*—José G. Dees
*Assistant Examiner*—Samuel Barts
*Attorney, Agent, or Firm*—Norbert Gruenfeld

[57] ABSTRACT

Disclosed are compounds of formula

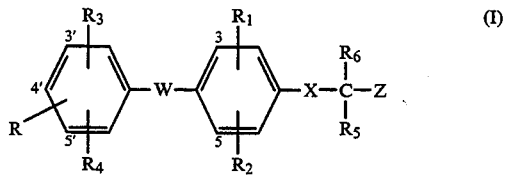

(I)

wherein
R is hydroxy, esterified hydroxy or etherified hydroxy;
$R_1$ is halogen, trifluoromethyl or lower alkyl;
$R_2$ is halogen, trifluoromethyl or lower alkyl;
$R_3$ is halogen, trifluoromethyl, lower alkyl, aryl, aryl-lower alkyl, cycloalkyl or cycloalkyl-lower alkyl; or
$R_3$ is the radical

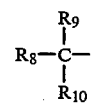

wherein $R_8$ is hydrogen, lower alkyl, aryl, cycloalkyl, aryl-lower alkyl or cycloalkyl-lower alkyl; $R_9$ is hydroxy or acyloxy; $R_{10}$ represents hydrogen or lower alkyl; or $R_9$ and $R_{10}$ together represent oxo;

$R_4$ is hydrogen, halogen, trifluoromethyl or lower alkyl;

X is $-NR_7$, S or O;

W is O or S;

$R_5$ represents hydrogen, lower alkyl or aryl-lower alkyl; and $R_6$ represents hydrogen; or $R_5$ and $R_6$ together represent oxo provided that X represents $-NR_7$;

$R_7$ represents hydrogen or lower alkyl;

Z represents carboxyl, carboxyl derivatized as a pharmaceutically acceptable ester or as a pharmaceutically acceptable amide; and pharmaceutically acceptable salts thereof; which are useful as hypocholesteremic agents.

15 Claims, No Drawings

HETEROACETIC ACID DERIVATIVES

CROSS-REFERENCE TO RELATED APPLICATIONS

This application is a continuation-in-part of application Ser. No. 07/918,544, filed Jul. 21, 1992, now abandoned which is incorporated herein by reference.

SUMMARY OF THE INVENTION

The invention relates to the heteroacetic acid derivatives as defined herein which are particularly useful as potent lipid lowering agents, methods for preparation thereof, pharmaceutical compositions comprising said compounds, and a method of treating hyperlipidemia, in particular hypercholesterolemia and related conditions in mammals, by administering said compounds or pharmaceutical compositions comprising said compounds.

The compounds of the invention are selective thyromimetic hypolipidemic agents which enhance the clearance of cholesterol from the circulation, particularly the clearance of cholesterol in the form of low density lipoproteins (LDL). They, inter alia, upregulate (increase) hepatic LDL receptor function in mammals.

Thus, the compounds of the instant invention are primarily useful for reducing total cholesterol plasma levels in mammals, in particular for reducing levels of LDL-cholesterol.

The compounds of the invention are therefore expected to be useful for the prevention and/or treatment of occlusive cardiovascular conditions in which hyperlipidemia and hyperlipoproteinemia are implicated, such as atherosclerosis and coronary heart disease (myocardial infarctions) in mammals.

DETAILED DESCRIPTION OF THE INVENTION

More particularly, the invention relates to the compounds of formula I

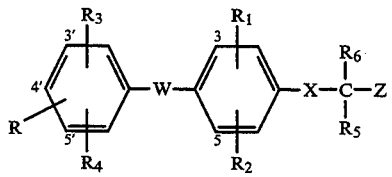

wherein

R is hydroxy, esterified hydroxy or etherified hydroxy;

$R_1$ is halogen, trifluoromethyl or lower alkyl;

$R_2$ is halogen, trifluoromethyl or lower alkyl;

$R_3$ is halogen, trifluoromethyl, lower alkyl, aryl, aryl-lower alkyl, cycloalkyl or cycloalkyl-lower alkyl; or $R_3$ is the radical

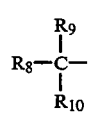 (a)

wherein $R_8$ is hydrogen, lower alkyl, aryl, cycloalkyl, aryl-lower alkyl or cycloalkyl-lower alkyl; $R_9$ is hydroxy or acyloxy; $R_{10}$ represents hydrogen or lower alkyl; or $R_9$ and $R_{10}$ together represent oxo;

$R_4$ is hydrogen, halogen, trifluoromethyl or lower alkyl;

X is —$NR_7$, S or O;

W is O or S;

$R_5$ represents hydrogen, lower alkyl or aryl-lower alkyl; and $R_6$ represents hydrogen; or $R_5$ and $R_6$ together represent oxo provided that X represents —$NR_7$;

$R_7$ represents hydrogen or lower alkyl;

Z represents carboxyl, carboxyl derivatized as a pharmaceutically acceptable ester or as a pharmaceutically acceptable amide; and pharmaceutically acceptable salts thereof.

Particular embodiments of the invention relate to the compounds of formula I wherein (a) R is located at the 4'-position; $R_1$ and $R_2$ are located at the 3 and 5 positions, and $R_3$ and $R_4$ are located at the 3' and 5'-positions;

(b) X and W represent O; or (c) X represents —$NR_7$, and W represents O; or (d) X represents S, and W represents O;

(e) $R_4$ is hydrogen;

(f) Z is carboxyl or carboxyl esterified as a pharmaceutically acceptable ester, (g) $R_5$ and $R_6$ together represent oxo and X represents $NR_7$;

(h) $R_3$ represents the radical

lower alkyl, aryl-lower alkyl or cycloalkyl-lower alkyl.

A preferred embodiment of the invention relates to the compounds of formula II

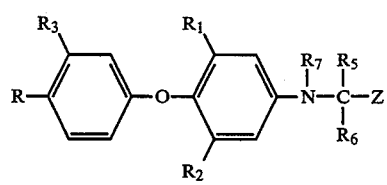

wherein R is hydroxy, esterified hydroxy or etherified hydroxy; $R_1$ and $R_2$ independently represent halogen, trifluoromethyl or $C_1$–$C_3$alkyl; $R_3$ represents lower alkyl, lower alkanoyl, hydroxy-lower alkyl, carbocyclic arylmethyl, carbocyclic aroyl or carbocyclic arylhydroxymethyl; $R_5$ and $R_6$ together represent oxo; $R_7$ represents hydrogen or lower alkyl; and Z represents carboxyl or carboxyl derivatized in form of a pharmaceutically acceptable ester or amide; and pharmaceutically acceptable salts thereof.

A further preferred embodiment relates to the compounds of formula III

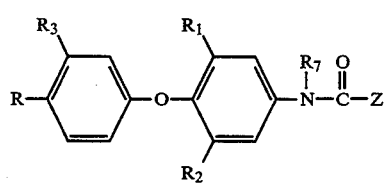

wherein R is hydroxy, esterified hydroxy or etherified hydroxy; $R_1$ represents halogen, trifluoromethyl or $C_1$-$C_3$alkyl; $R_2$ represents halogen, trifluoromethyl or $C_1$-$C_3$alkyl; $R_3$ represents lower alkyl, carbocyclic aroyl, carbocyclic arylmethyl or carbocyclic aryl-hydroxymethyl; $R_7$ represents hydrogen or lower alkyl; Z represents carboxyl or carboxyl derivatized as a pharmaceutically acceptable ester or amide; and pharmaceutically acceptable salts thereof.

Advantageously Z represents carboxyl or carboxyl esterified as a pharmaceutically acceptable ester.

Preferred are said compounds of formula III wherein R is hydroxy, lower alkanoyloxy, lower alkoxy or tetrahydropyranyloxy; $R_1$ and $R_2$ are advantageously identical and represent halogen or $C_1$-$C_3$-alkyl; $R_3$ is $C_1$-$C_3$-alkyl or monocyclic carbocyclic arylmethyl; $R_7$ is hydrogen or $C_1$-$C_2$-alkyl; Z is carboxyl or carboxyl derivatized as a pharmaceutically acceptable ester or amide; and pharmaceutically acceptable salts thereof.

A further preferred embodiment relates to compounds of formula III wherein R is hydroxy, lower alkanoyloxy, lower alkoxy or tetrahydropyranyloxy; $R_1$ and $R_2$ are advantageously identical and represent halogen or $C_1$-$C_3$-alkyl; $R_3$ is carbocyclic aroyl or carbocyclic aryl-hydroxymethyl; $R_7$ is hydrogen or $C_1$-$C_2$alkyl; Z is carboxyl or carboxyl derivatized as a pharmaceutically acceptable ester or amide; and pharmaceutically acceptable salts thereof.

Further preferred are said compounds of formula III wherein R is hydroxy; $R_1$ and $R_2$ are advantageously identical and represent chloro or methyl; $R_3$ is isopropyl, benzyl or benzyl substituted by halogen, lower alkyl, lower alkoxy or trifluoromethyl; $R_7$ is hydrogen; Z is carboxyl or lower alkoxycarbonyl; and pharmaceutically acceptable salts thereof.

Particularly preferred are also compounds of formula III wherein R is hydroxy; $R_1$ and $R_2$ are identical and represent chloro or methyl; $R_3$ is phenyl-hydroxymethyl or phenyl-hydroxymethyl substituted on phenyl by halogen, lower alkyl, lower alkoxy or trifluoromethyl; or $R_3$ is benzoyl or benzoyl substituted by halogen, lower alkyl, lower alkoxy or trifluoromethyl; $R_7$ is hydrogen; Z is carboxyl or lower alkoxycarbonyl; and pharmaceutically acceptable salts thereof.

Particularly preferred are also compounds of formula III wherein R is hydroxy; $R_1$ and $R_2$ are identical and represent methyl or chloro; $R_3$ is isopropyl or 4-halophenyl-hydroxymethyl in which halo represents fluoro or chloro; $R_7$ is hydrogen; and Z represents carboxy or lower alkoxycarbonyl; and pharmaceutically acceptable salts thereof.

Another particular embodiment of the invention relates to the compounds of formula IV

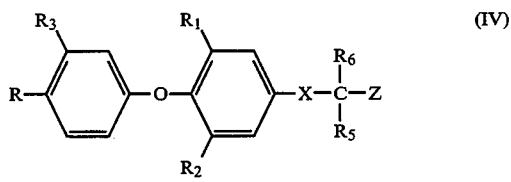

wherein R is hydroxy, esterified hydroxy or etherified hydroxy; $R_1$ and $R_2$ independently represent halogen, trifluoromethyl or $C_1$-$C_3$alkyl; $R_3$ represents lower alkyl, carbocyclic arylmethyl, carbocyclic aroyl, or carbocyclic aryl-hydroxymethyl; X represents $NR_7$, S or O; $R_5$, $R_6$ and $R_7$ independently represent hydrogen or lower alkyl; Z represents carboxyl or carboxyl derivatized as a pharmaceutically acceptable ester or as a pharmaceutically acceptable amide; and pharmaceutically acceptable salts thereof.

Preferred are said compounds wherein $R_5$, $R_6$ and $R_7$ represent hydrogen; also said compounds wherein Z represents carboxyl or carboxyl esterified as a pharmaceutically acceptable ester, and pharmaceutically acceptable salts thereof.

Certain compounds of the invention which have one or more asymmetric centers can exist in the form of racemates, enantiomers and mixtures thereof, all of which are within the scope of the invention.

The definitions used herein, unless denoted otherwise, have the following meanings within the scope of the present invention.

Aryl represents carbocyclic or heterocyclic aryl.

Carbocyclic aryl represents optionally substituted phenyl or optionally substituted naphthyl.

Optionally substituted phenyl represents preferably phenyl or phenyl substituted by one to three substituents, such being advantageously lower alkyl, hydroxy, lower alkoxy, lower alkanoyloxy, halogen, cyano, trifluoromethyl, lower alkanoylamino or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl or halogen.

Optionally substituted thienyl represents 2- or 3-thienyl or 2- or 3-thienyl preferably substituted by lower alkyl.

Aryl as in aryl-lower and the like is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

Aryl-lower alkyl is advantageously benzyl or phenethyl optionally substituted by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Cycloalkyl represents a saturated cyclic hydrocarbon radical, preferably $C_5$-$C_7$-cycloalkyl which contains 5 to 7 ring carbons and is, advantageously cyclopentyl or cyclohexyl.

Cycloalkyl-lower alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Lower alkenyloxy represents preferably alkyloxy.

Di-lower alkylamino preferably contains 1–4 carbon atoms in each lower alkyl portion and represents, for example, N,N-dimethylamino, N-methyl-N-ethylamino and advantageously N,N-diethylamino.

Lower alkoxycarbonyl preferably contains 1 to 4 carbon atoms in the alkoxy portion and represents, for example, methoxycarbonyl, propoxycarbonyl, isopropoxycarbonyl or advantageously ethoxycarbonyl.

Hydroxy-lower alkyl is preferably hydroxymethyl.

Halogen (halo) preferably represents fluoro or chloro, but may also be bromo or iodo.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl represents preferably lower alkanoyl, carbocyclic aryl-lower alkanoyl or carbocyclic aroyl.

Carboxyl derivatized as a pharmaceutically acceptable ester represents esterfied carboxyl, advantageously a prodrug ester that may be convertible by solvolysis or under physiological conditions to the free carboxylic acid, such being preferably lower alkoxycarbonyl; (amino, acylamino, mono- or di-lower alkylamino)-lower alkoxycarbonyl; carboxy- lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkyl-piperazino)-carbonyl-lower alkoxycarbonyl; carbocyclic or heterocyclic aryl-lower alkoxycarbonyl, preferably optionally (halo, lower alkyl or lower alkoxy)-substituted benzyloxycarbonyl, or pyridylmethoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, advantageously being (2,2-dimethyl-1,3-dioxolan-4-yl)-methoxycarbonyl.

Carboxyl derivatized as a pharmaceutically acceptable prodrag ester represents most advantageously $C_1$–$C_4$-alkoxycarbonyl, benzyloxycarbonyl optionally substituted on phenyl by lower alkyl, lower alkoxy, halo or trifluoromethyl, 1-($C_2$–$C_4$-alkanoyloxy)-ethoxycarbonyl, (2,2-dimethyl- 1,3-dioxolan-4-yl)-methoxycarbonyl, 5-indanyloxycarbonyl, 1-($C_1$–$C_4$-alkoxycarbonyloxy)-ethoxycarbonyl or 3-pyridylmethoxycarbonyl.

Carboxyl derivatized as a pharmaceutically acceptable amide represents preferably carbamoyl or N-substituted carbamoyl, advantageously [lower alkylamino, arylamino, di-lower alkylamino, morpholino, N-lower alkylpiperazino, pyrrolidino, piperidino, (amino or acylamino)-lower alkylamino or aryl-lower alkylamino]-carbonyl.

Esterified hydroxy represents acyloxy, e.g. acyloxy derived from an organic carboxylic acid, preferably lower alkanoyloxy, aroyloxy, or aryl-lower alkanoyloxy; also 3,7,12(3α,5β, 7α, 12α)-trihydroxy-cholan-24-oyloxy (derived from cholic acid), and the like.

Etherified hydroxy represents preferably lower alkoxy, lower alkenyloxy, $C_5$–$C_7$-cycloalkyloxy, carbocyclic aryl-lower alkoxy, tetrahydropyranyloxy, $C_5$–$C_7$-cycloalkyl-lower alkoxy, and the like.

Pharmaceutically acceptable salts are either pharmaceutically acceptable acid addition salts for any basic compounds of the invention or salts derived from pharmaceutically acceptable bases for any acidic compounds of the invention.

Pharmaceutically acceptable salts of any basic compounds of the invention are acid addition salts, which are preferably such of therapeutically acceptable inorganic or organic acids, such as strong mineral acids, for example hydrohalic, e.g. hydrochloric, hydrobromic, sulfuric or phosphoric acid; aliphatic or aromatic carboxylic or sulfonic acids, e.g. acetic, propionic, succinic, glycollic, lactic, malic, tartaric, gluconic, citric, maleic, fumaric, pyruvic, phenylacetic, benzoic, pamoic, nicotinic, methanesulfonic, ethanesulfonic, hydroxyethanesulfonic, 1,2-ethanedisulfonic, benzenesulfonic, p-toluenesulfonic or naphthalenesulfonic acid; or ascorbic acid.

Pharmaceutically acceptable salts of the acidic compounds of the invention, e.g. those having a carboxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, dicthanolamine, triethanolamine, trimethamino salts).

The novel compounds of the invention have valuable pharmacological properties. They are pharmacologically potent hypolipidemic agents which reduce plasma cholesterol levels in mammals. The compounds of the invention demonstrate potent binding to the triiodothyronine ($T_3$) nuclear receptor which is indicative of upregulation of LDL receptor activity and enhancement of the clearance of LDL-cholesterol from the circulation.

The compounds of the invention are thus particularly useful in mammals as hypocholesteremic agents for the treatment and prevention of occlusive cardiovascular conditions in which hypercholestermia are implicated, by reducing plasma levels of total and LDL-cholesterol.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenteally, advantageously intravenously, e.g. as a suspension or in aqueous solution. The dosage in vitro may range between about $10^{-7}$ molar and $10^{-11}$ molar concentrations. The dosage in vivo may range depending on the route of administration, between about 0.1 and 300 micrograms/Kg, preferably between about 0.5 and 100 micrograms/Kg, advantageously between about 1 and 100 micrograms/Kg.

The in vitro binding to $T_3$ nuclear receptors is determined as follows:

Rat liver nuclei and plasma membrane preparations are obtained from Sprague-Dawley (CD) rats (Charles River Labs.) by differential centrifugation as described by Emroclot et al (Methods in Enzymology 31:75, Pan A, 1974) with minor modifications. The nuclear fraction obtained from the 275× g pellet is further purified as generally described by Spindler et al (*J. Biol. Chem.* 250:4118, 1975).

The novel test compounds are assayed for binding to the nuclei by the method of Spindler et al (*J. Biol. Chem.* 250:4118, 1975). The nuclei are incubated at 22° C. with 0.3 nM of [$^{125}$I]-L-triiodothyronine (L-T$_3$). Parallel incubations are conducted with tubes combining, in addition to the nuclei and radioactive L-T$_3$, either various concentrations of the test compounds or 3 μM of nonradioactive L-T$_3$. The latter is used as a measure of nonspecific binding. The radioactivity bound to the nuclei is detained following centrifugation of the reaction mixture at 800× g for 7 minutes and washing of the pellet obtained. The mount of [$^{125}$I-L-T$_3$ specifically bound is determined by subtracting the mount non-specifically bound (radioactivity contained in the nuclear pellet following incubation with excess (3 μM) non-radioactive L-T$_3$). The concentration of test compound which inhibits the specific binding of [$^{125}$I]-L-T$_3$ by 50 percent (IC$_{50}$) is determined graphically from the reciprocal plot of the specifically bound [$^{125}$I]-L-T$_3$ venus the various concentrations of the test compound.

Cholesterol lowering activity is determined in the rat as follows:

Male Sprague-Dawley rats (230–250 g) (Taconic Farms) are maintained ad libium on water and a high cholesterol diet (1.5% cholesterol and 0.5% cholic acid) for two weeks prior to and during the 7-day treatment period. Groups of animals are treated orally by gavage with the vehicle alone or with test compound for 7 consecutive days. After the host dose, animals are fasted for 18 hours and blood is collected. Blood samples are centrifuged at 2500 rpm for 10 minutes to prepare plasma for total cholesterol determination as well as LDL and HDL cholesterol concentrations. HDL values are determined after LDL/VLDL precipitation (Warnick and Albers, 1978). All samples are analyzed enzymatically for cholesterol with a diagnostic reagent kit (Sigma Chemical Co., St. Louis, MO). The analysis is performed on a Bio-Mek automated work station. LDL/VLDL fractions are precipitated in the following manner: 0.35 ml of plasma is aliquoted into Eppendorf tubes to which 12 μl of 2M manganese chloride, 11.2 μl of sodium heparin (Porcine Intestinal, 5000 units/ml), and 8.3 μl of normal saline are added. The samples are vortexed and are placed on ice for 15 minutes, then centrifuged at 4° C. for 10 minutes at 1300 rpm and the supernatant is enzymatically analyzed for cholesterol. The HDL cholesterol concentration is adjusted for dilution by multiplying the supernatant cholesterol value by 1.09. LDL/VLDL cholesterol values are obtained by subtracting HDL cholesterol from total cholesterol.

Cholesterol-lowering activity can also be evaluated in normocholesterolemic dogs fed regular chow following the procedure described above, by administration of test compound orally for 5 days; also in normolipomic cynomolgus monkeys.

Illustrative of the invention, N-[3,5-dimethyl-4-(4'-hydroxy-3'-isopropylphenoxy)phenyl]oxamic acid demonstrates an IC$_{50}$ of about 0.2 nM in the T$_3$ nuclear receptor binding assay. Furthermore, said compound significantly lowers sen cholesterol at a daily dose of about 20 micrograms (μg)/Kg p.o. in the rat and about 30 μg/Kg p.o. in the dog. As a further illustration, ethyl N-[4-[3'-[(4-fluorophenyl)hydroxymethyl]4'-hydroxyphenoxy]-3,5dimethylphenyl]oxamate (IC$_{50}$=0.1 nM) significantly lowers serum cholesterol at a daily dose of about 5 μg/Kg p.o. in the rat, of about 10 μg/Kg p.o. in the dog and of about 1 μg/Kg p.o. in the monkey.

The compounds of the invention can be prepared by condensing a compound of the formula

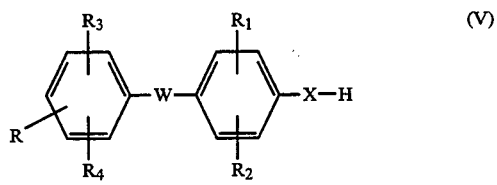

wherein R, R$_1$–R$_4$, W and X have meaning as defined hereinabove, advantageously with a reactive functional derivative of a compound of the formula VI or VII

or

wherein R$_5$, R$_6$ and Z have meaning as defined hereinabove, in protected form as required; and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic function into a pharmaceutically acceptable ester or amide derivative, or converting a resulting ester or amide into the free acid or into another ester or amide derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in a manner described herein, functional groups present, such as carboxyl, amino and hydroxy groups, are optionally protected by conventional protecting groups that arc common in preparative organic chemistry. Protected carboxyl, amino and hydroxy groups are those that can be converted under mild conditions into free carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (hydroxy, carboxyl group, amino group etc.), the structure and stability of the molecule of which the substituent is a part, and the reaction conditions.

Well-known protecting groups that meet these conditions and their introduction and removal are described, for example, in J.F.W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York, 1965.

Reactive functional derivatives of compounds of formula VI represent hydroxy esterified by a strong inorganic or organic acid and are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

Reactive functional derivatives of compounds of formula VII (oxalic acid derivatives) are preferably halides, mixed anhydrides such as the pivaloyl or alkoxycarbonyl arthydride, and esters such as lower alkyl esters.

The condensation (alkylation or acylation), according to the above process, of a compound of formula V with a reactive functional derivative of a compound of formula VI or of formula VII is carried out according to methodology well-known in the art, by reacting such without solvent at elevated temperature, or in an inert solvent, such as dimethylformamide or methylene chloride, advantageously in the presence of a base, such as potassium carbonate, triethylamine, diisopropylethylamine, pyridine and the like at room or elevated temperature.

For example, relating to the preparation of compounds wherein $R_5$ and $R_6$ together represent oxo, a compound of formula V in which XH represents e.g. $NH_2$, is condensed with an ester or amide derivative of oxalic acid, such as diethyl oxalate (the reactive derivative of a compound of formula VII), using diethyl oxalate as both reagent and solvent, at elevated temperature. Alternatively, a hemiester-hemihalide of oxalic acid, e.g. ethyl oxalyl chloride can be used as the reactive derivative of a compound of formula VII, and the condensation is carried out e.g. in an inert solvent, such as methylene chloride, and in the presence of a base, such as potassium carbonate or triethylamine. If a hemiester-hemiamide of oxalic acid is used, the corresponding amide is obtained.

The starting materials of formula VI and VH are either known or can be prepared according to methods known in the art.

The starting materials of formula V wherein XH represents $NH_2$ can e.g. be prepared by (a) condensing a 4-nitrophenol (or corresponding thiophenol) appropriately substituted by $R_1$ and $R_2$ of the formula VII

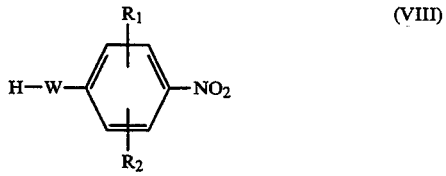

(VIII)

wherein $R_1$, $R_2$ and W have meaning as defined hereinabove, with a bis-aryl iodonium tetrafluoroborate appropriately substituted by $R'$, $R_3'$ and $R_4'$ of the formula IX

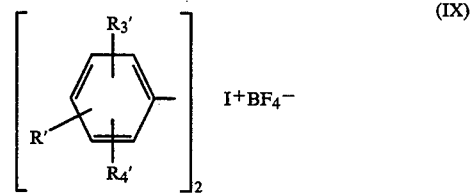

(IX)

wherein $R'$, $R_3'$ and $R_4'$ represent R, $R_3$ and $R_4$ as defined hereinabove, or $R'$, $R_3'$ and $R_4'$ are groups convertible to R, $R_3$ and $R_4$, respectively, in the presence of e.g. copper, a base such as triethylamine and an inert solvent such as methylene chloride; or (b) condensing a 4-chloronitrobenzene appropriately substituted by $R_1$ and $R_2$ of the formula

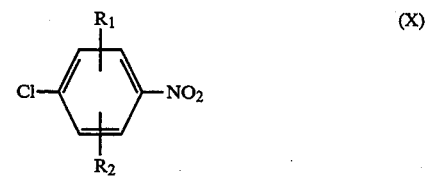

(X)

with a phenol (or thiophenol) appropriately substituted by $R'$, $R_3'$ and $R_4'$ of the formula

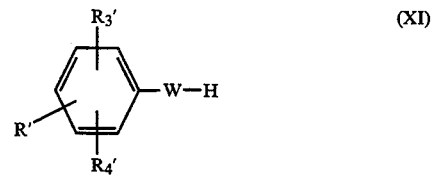

(XI)

wherein $R'$, $R_3'$, $R_4'$ and W have meaning as defined hereinabove in the presence of a base, such as potassium carbonate in a polar inert solvent such as dimethylsulfoxide or N-methylpyrrolidone; and (c) reducing a resulting compound of the formula XII

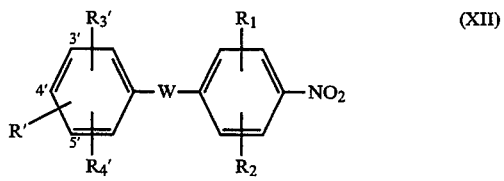

(XII)

wherein $R'$, $R_1$, $R_2$, $R_3'$, $R_4'$ and W have meaning as defined hereinabove, e.g. by catalytic hydrogenation in the presence of e.g. Raney nickel or palladium on charcoal as catalyst, in a polar solvent, such as glacial acetic acid or ethanol, to obtain an amine intermediate of formula V or an amine intermediate convertible to an amine intermediate of formula V.

The bis-aryl iodonium tetrafluoroborates of formula IX, e.g. wherein $R'$ represents 4'-alkoxy or 4'-benzyloxy (which may be further substituted by e.g. lower alkyl) can be prepared e.g. by condensation of the corresponding optionally substituted anisole or benzyloxy benzene with di-(trifluoroacetyl)-iodonium tetrafluoroborate (prepared from iodine, nitric acid, acetic anhydride, trifluoroacetic acid and sodium tetrafluoroborate) according to methods known in the art and illustrated herein.

A 4-chloronitrobenzene of formula X can be prepared from the corresponding 4-nitrophenol of formula VII by first converting such to e.g. the trifluoromethylsulfonyl ester, and treating the latter with lithium chloride in an inert solvent such as N-methylpyrrolidone or dimethylformamide. The 4-methylphenol can in turn be prepared by nitration of the phenol under conditions well-known in the art, e.g. with nitric acid in acetic acid or with nitronium tetrafluoromborate.

The appropriately substituted phenols and thiophenols of formula XI are known in the art or are prepared as illustrated herein.

For example, a compound of formula XI can be prepared by Fries type rearrangement of an acetic acid ester of the appropriately substituted phenol with e.g. aluminum chloride to obtain the appropriately substituted hydroxyacetophenone, which is protected as an ether, and subsequently oxidized under Baeyer-Villiger conditions, e.g. with pencetic acid to the acetic acid ester of the substituted phenol, which is then hydrolyzed to the phenol of formula XI.

Intermediates of formula XII wherein R' represents e.g. 4'-lower alkoxy or 4'-benzyloxy, and $R_3'$ and $R_4'$ are hydrogen, can be converted to intermediates of formula XII wherein $R_3'$ is the radical 3'-$R_8$—CO— and $R_8$ has meaning as defined hereinabove, by treating a said intermediate of formula XII under Friedel-Crafts acylation conditions with a reactive derivative of a carboxylic acid $R_8$-COOH, such as the acid chloride or anhydride, in the presence of a Lewis acid.

For example, acylation of a compound of formula XII wherein R' is 4'-alkoxy or 4'-benzyloxy, and $R_3'$ and $R_4'$ represent hydrogen, with an aroyl chloride, such as optionally substituted benzoyl chloride in the presence of titanium chloride in methylene chloride yields the corresponding compound of formula XII wherein R' is 4'-alkoxy or 4'-benzyloxy, $R_3'$ is 3'-aroyl, and $R_4'$ is hydrogen.

Subsequent conversion to a compound of formula XII wherein R' is 4'-hydroxy is achieved according to methods well known in the art, e.g. with acid such as hydrochloric acid or a boron trihalide, such as boron trichloride or boron tribromide when R' is in particular 4'-methoxy.

Intermediates, e.g. of formula XII, wherein $R_3'$ is aroyl can be reduced to corresponding compounds wherein $R_3'$ is arylmethyl by reduction with e.g. triethylsilane and trifluoroacetic acid in methylene chloride.

Intermediates, e.g. of formula XII, wherein $R_3'$ is e.g. aroyl can be reduced to the corresponding compounds wherein $R_3'$ is aryl-hydroxymethyl using e.g. an alkali metal borohydride such as sodium or lithium borohydride in a polar solvent such as methanol or acetic acid. Said ketone intermediate, of formula XII, wherein $R_3'$ represents e.g. aroyl can also be reduced by catalytic hydrogenation to obtain the corresponding amine intermediates of formula V wherein XH represents $NH_2$ and $R_3$ represents aryl-hydroxymethyl.

Intermediates of formula V wherein XH represents $NH_2$ can be converted to the corresponding thiophenol intermediates of formula V wherein XH represents SH by first diazotization of the amines to the diazonium salts, which are then reacted with e.g. potassium O-ethylxanthate to obtain first the ethyl xanthate derivatives which are hydrolyzed to the corresponding thiophenol intermediates of formula V wherein XH represents SH. Furthermore, hydrolysis of the cliazonium salts, e.g. as described in organic synthesis Coll. Vol. 3, 130 (1955), leads to the phenolic intermediates of formula V wherein XH represents OH.

The intermediates of formula V wherein XH represents $NH_2$ may be converted to intermediates wherein XH represents $NHR_7$ according to methods well-known in the art for conversion of a primary to a secondary amine, such as by reductive alkylation. In the case where $R_7$ represents methyl, the transformation can be accomplished e.g. by treatment with ethyl chloroformate followed by reduction with lithium aluminum hydride.

The compounds of the invention can be convened into each other according to conventional methods. Thus, for example, resulting amides or esters may be hydrolyzed with aqueous alkalides, such as alkali metal carbonates or hydroxides. Resulting free acids may be esterified with e.g. said unsubstituted or substituted alkanols or reactive esterified derivatives thereof such as alkyl halides, or diazoalkanes. Free acids are also converted into said metal, ammonium or acid addition salts in conventional manner.

Thus, any resulting free acid can be converted into a corresponding metal, ammonium or acid addition salt respectively, by reacting it with an equivalent mount of the corresponding base, or ion exchange preparation, e.g. said free acids with alkali or ammonium hydroxides or carbonates. Any resulting salt may also be converted into the free compound, by liberating the latter with stronger acids. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization. Furthermore, the functional derivatives of the free acids of formula I, e.g. wherein carboxy is esterified may be prepared by condensing a free acid of formula I with an esterifying agent of the formula XIII $$R_9-Y \qquad (XIII)$$

wherein Y represents hydroxy or a reactive esterified hydroxyl group; and $R_9$ represents an esterifying radical as defined herein for the esters (esterified carboxy).

A reactive esterified hydroxyl group, such as Y in a compound of the formula XIII, is a hydroxyl group esterified by a strong inorganic or organic acid. Corresponding Y groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The esterification of the carboxyl group, optionally in salt form, with a compound of formula XIII wherein Y represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-diisopropylamine, an N,N-di-lower-alkyl-aniline, for example N,N-di-methylaniline, a cyclic tertiary mine, such as an N-lower-alicylated morpholine, for example N-methyl-morpholine, a base of the pyridine type, for example pyridine, an inorganic base, for example hydroxides, carbonates, or hydrogen carbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

Esterification of a compound with a free carboxyl group using in excess an alcohol of formula XIII (wherein Y represents hydroxy) is carried out in a manner known per se, e.g. in the presence of an acid catalyst e.g. sulfuric acid or boron trifluoride etherate, preferably at an elevated temperature, advantageously ranging from about 40° C. to 100° C. Alternatively, the esterification of a compound with a free carboxyl group can be carried out with at least an equimolar amount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Similarly, the free carboxylic acids can be converted to amides using methods well known in the art, e.g. in the presence of a condensing agent such as 2-ethoxy-1-ethoxycarbonyl-1,2-dihydroquinoline Conversely, carboxylic acid esters can be converted to compounds of the invention with a free carboxy group using the methods and conditions generally known in the art and illustrated herein. Depending on type of ester involved, useful reagents include aqueous acids or bases. Any benzyl esters can be selectively hydrogenolyzed with e.g. hydrogen in the presence of a catalyst such as palladium on charcoal.

Compounds wherein R represents esterified hydroxy or etherified hydroxy can be converted to the compounds wherein R represents hydroxy using methods well-known in the art.

For example, compounds wherein R represents e.g. methoxy can be treated with boron tribromide or boron trichloride in e.g. dichloromethane to obtain compounds wherein R is hydroxy. Also, if R represents benzyloxy, such can be debenzylated by hydrogenolysis with hydrogen in the presence of e.g. palladium catalyst. In the case of esterified hydroxy such can be deesterified with e.g. aqueous acid or base, such as lithium or sodium hydroxide.

In the case mixtures of stereoisomers or optical isomers are obtained, these can be separated into the single isomers by methods in themselves known, e.g., by fractional distillation, crystallization and/or chromatography. Racetalk products or intermediates can be resolved into the optical antipodes, for example, by separation of diasteromeric salts thereof, e.g. for basic compounds by the fractional crystallization of d- or l-(tartrate, mandelate or camphorsulfonate) salts, or for acidic compounds by franctional crystallization of d- or 1-(alpha-methylbenzylamine, cinchonidine, cinchonine, quinine, quinidine, ephedrine, dehydroabietylamine, brucine or strychnine)-salts. Racetalc products can also be resolved by chiral chromatography, e.g. high pressure liquid chromatography using a chiral adsorbent.

The above-mentioned transformations are carried out according to standard methods for the reactions involved, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The present invention additionally relates to the use in mammals for the treatment of hypercholesterolemia of the compounds of the invention or pharmaceutical compositions thereof, e.g. as cholesterol lowering agents, e.g. for lowering LDL-cholesterol, by administration to a mammal in need thereof of a therapeutically effective amount of a said compound.

The pharmaceutical compositions according to the invention are those suitable for enteral, such as oral or rectal, transdermal and parenteral administration to mammals, including man, for the treatment of hypercholesterolemia, comprising an effective amount of a pharmacologically active compound of the invention, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application.

Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrilidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carder. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 0.01 mg and 10 mg of the active ingredient. The dosage of active compound is dependent on the species of warm-blooded animal (mammal), the body weight, age and individual condition, on the form of administration, and on the compound involved.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Reduced pressures are expressed as mmHg or Torr. Hydrogenation pressers are indicated as atmospheres or psi (pounds/square inch). Other abbreviations are those standard in the art.

EXAMPLE 1

To 3,5-dimethyl-4-(3'-isopropyl-4'-methoxyphenoxy)-aniline (5.8 g) is added 37.5 g of dimethyl oxalate and this mixture is stirred at 120° for 4 hours Excess dimethyl oxalate is removed under high vacuum in a hot water bath and the residue is chromatographed on silica gel using 95:5 to 90:10 toluene:ethyl acetate as eluent to yield crude product which is crystallized from toluene to give methyl N-[3,5-dimethyl-4-(4'-methoxy-3'-isopropylphenoxy)-phenyl]oxamate. NMR (CDCl$_3$):$\delta$1.1 (6H,d), 2.1 (6H, s), 3.2 (1H,m), 3.7 (3H, s), 4.0 (3H, s), 6.3 (1H,d of d), 6.6 (1H,d), 6.7 (1H,d), 7.3 (2H, s) 8.7 (1H, s). The structure formula is

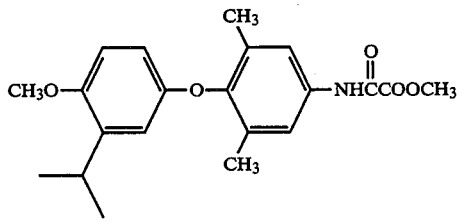

The starting material is prepared as follows:

2-Isopropylphenol (300 g), 262 ml of dimethyl sulfate, and 1500 g of potassium carbonate in 1 liter of acetone are stirred mechanically and refluxed for 6½ hours. The mixture is filtered and the filter cake washed with acetone. The combined filtrate is stripped, the residue is redissolved in ether, then extracted with 2N sodium hydroxide (twice) and brine (once). The ether is dried, filtered, and stripped to leave an oil which is distilled under high vacuum to afford 2-isopropylanisole, b.p. 39°.

Concentrated nitric acid (>90%, 12.4 ml) is added dropwise to 31.4 ml acetic anhydride chilled in dry ice/carbon tetrachloride. Iodine (11.26 g) is added in one portion followed by 20.5 ml of trifluoroacetic acid dropwise. The mixture is stirred at room temperature until all the iodine dissolves and nitrogen oxides are then purged with nitrogen gas. The solution is then stripped under high vacuum at <40° to give a solid which is redissolved in 126 ml acetic anhydride and recooled in dry ice/carbon tetrachloride. 2-Isopropylanisole (40 g), 151 ml acetic anhydride, and 22.6 ml trifluoroacetic acid are added dropwise and the solution obtained is allowed to stand in a refrigerator overnight. This solution is stripped under high vacuum at <40°, taken up in 150 ml methanol, and treated with 150 ml of 10% (w/v) sodium bisulfite and 1 liter of 2F sodium tetrafluoroborate. When the precipitate has aggregated the supernatant is decanted and the residue trimmed with hexane to give crystals which are filtered, washed with hexane, and dried at room temperature in vacuo to afford bis-(3-isopropyl-4-methoxyphenyl) iodonium tetrafluoroborate.

Bis (3-Isopropyl-4-methoxyphenyl) iodonium tetrafluoroborate (116.5 1 g) and 19.26 g of copper bronze are stirred in 300 ml dichloromethane cooled in an ice water bath. A mixture of 25.36 g of 2,6-dimethyl-4-nitrophenol and 16.88 g of triethylamine is added dropwise. The mixture is stirred in the dark for five days, then filtered through Celite to remove copper. The filtrate is stripped and the residue chromatographed on silica gel with 97:3 hexane:ethyl acetate as eluent, affording 3,5-dimethyl-4-(3'-isopropyl-4'-methoxyphenoxy)-nitrobenzene NMR(CDCl$_3$): $\delta$1.1 (6H,d), 2.2 (6H,s), 3.3 (1H,m), 3.7 (3H,s), 6.3 (1H,d of d), 6.6 (1H,d), 6.7 (1H,d), 8.0 (2H,s).

3,5-Dimethyl-4-(3'-isopropyl-4'-methoxyphenoxy)-nitrobenzene can also be prepared as follows:

2,6-Dimethyl-4-nitrophenol (5.00 g) and 6.05 ml pyridine in 50 ml dichloromethane are cooled in an ice/salt bath and 6.04 ml of trifluoromethanesulfonic anhydride is added over 30 minutes. After stirring cold for an hour the mixture is quenched with 25 ml water, the layers separated, and the organic phase successively washed with 2N hydrochloric acid (twice), water (twice), 2N sodium hydroxide, and water (twice). Solvent is dried, filtered, and stripped to afford 2,6-dimethyl-4-nitrophenyl trifluoromethanesulfonate. NMR (CDCl$_3$): $\delta$2.5 (6H, s), 8.0 (2H, s).

2,6-Dimethyl-4-nitrophenyl trifluoromethanesulfonate (8.54 g) and 3.63 g of lithium chloride in 40 ml DMF are heated at 150° for four hours. Solvent is then evaporated, the residue stirred with water and ethyl acetate, filtered, and the filtrate separated. The ethyl acetate is then dried, filtered and stripped, and the residue chromatographed on silica gel with 98:2 hexane:ethyl acetate, affording 4-chloro-3,5-dimethyl-nitrobenzene. NMR (CDCl$_3$): $\delta$2.5 (6H,s), 7.9 (2H,s).

4-Chloro-3,5-dimethylnitrobenzene (2.12 g), 1.9 g of 3-isopropyl-4-methoxyphenol, and 1.74 g of potassium carbonate are heated 18 hrs at 125° in 25 ml dimethylsulfoxide. The mixture is poured into ethyl acetate and extracted once with water and five times with brine. The ethyl acetate is dried, filtered, and stripped to yield an oil which is chromatographed on silica gel with 97:3 hexane:ethyl acetate to afford 3,5-dimethyl-4-(3'-isopropyl-4'-methoxyphenoxy)-nitro benzene NMR (CDCl$_3$): $\delta$1.1 (6H,d), 2.2 (6H,s), 3.3 (1H,m), 3.7 (3H, s) 6.3 (1H,d of d), 6.6 (1H,d), 6.7 (1H, d), 8.0 (2H, s).

3,5-Dimethyl-4-(3'-isopropyl-4'-methoxyphenoxy)-nitrobenzene (6.0 g) and 600 mg of 10% platinum on carbon in 200 ml ethanol are hydrogenated on a Parr shaker. Catalyst is removed by filtration through Celite and the filtrate is stripped to afford 3,5-dimethyl4-(3'-isopropyl-4'-methoxyphenoxy)-aniline.

EXAMPLE 2

(a) To 10 g of methyl N-[3,5-dimethyl-4-(4'-methoxy-3'-isopropylphenoxy)phenyl]-oxamate in 150 ml. dichloromethane cooled in dry ice/acetone is added 54 ml of 1M boron tribromide in dichloromethane. The bath is then removed and after stirring overnight the mixture is poured into ice. The layers are separated and the aqueous phase is extracted with ethyl acetate twice. The combined organic phases are dried, filtered, and stripped to give crude acid. Reesterification is effected by dissolving such in 100 ml dimethylformamide, cooling in an ice bath, and treating with 9.15 g. cesium carbonate and 2.66 ml dimethyl surface. After stirring at ambient overnight, the mixture is decanted into ethyl acetate and washed six times with brine. The organic phase is dried, filtered, and stripped to give an oil which is chromatographed on silica gel with 90:10 to 75:25 hexane:ethyl acetate to give methyl N-[3,5-dimethyl4-(4'-hydroxy-3'-isopropylphenoxy)-phenyl]-oxamate.

(b) 1.0N Sodium hydroxide (51 ml) is added to 8.70 g of methyl N-[3,5-dimethyl-4-(4'-hydroxy-3-isopropylphenoxy)-phenyl]oxamate in 125 ml methanol, the mixture is refluxed 30 minutes, then cooled to room temperature. Solvent is evaporated, the residue dissolved in water, and extracted with ether twice. The aqueous layer is chilled in ice and acidified with concentrated hydrochloric acid. The resulting solid is collected, dissolved in ethyl acetate and the solution dried, filtered, and stripped. The residue is crystallized from toluene to give N-[3,5-dimethyl-4-(4'-hydroxy-3'-isopropylphenoxy)-phenyl]oxamic acid, m.p. 183°–185°.

EXAMPLE 3

3,5-Dimethyl-4-(3'-isopropyl-4'-methoxyphenoxy)-aniline (10.8 g) is fused at 120° for 4 hours with 50 g. of ethyl oxamate. The cooled mixture is twice triturated with hot water, then stirred with ethyl acetate, filtered to remove insolubles, and the ethyl acetate dried, filtered, and stripped to afford an oily solid. Purification is effected by chromatography on silica gel with 95:5 to 80:20 toluene:ethyl acetate as eluent to give N-[3,5-dimethyl-4-(4'-methoxy-3'-isopropylphenoxy)-phenyl]-oxamide. NMR (D$_3$COD): δ 1.1 (6H,d), 2.1 (6H,S), 3.2 (1H, m), 3.8 (3H,s), 6.4 (1H,d of d), 6.7 (1H, d), 6.8 (1H, d), 7.5 (2H,s).

The starting material is prepared as follows:

3,5-Dimethyl-4-(3'-isopropyl-4'-methoxyphenoxy)nitrobenzene (480 mg) and 50 mg of 10% platinum on carbon in 100 ml ethanol are reduced on a Parr shaker. Catalyst is removed by filtration through Celite and the filtrate stripped. The residue is taken up in ether and acidified with gaseous hydrogen chloride. The ether solution is chilled, filtered to remove insolubles, and stripped to afford 3,5-dimethyl-4-(3'-isopropyl-4'-methoxyphenoxy)-aniline hydrochloride, m.p. 95°–100°.

EXAMPLE 4

N-[3,5-Dimethyl4-(4'-methoxy-3'-isopropylphenoxy)-phenyl]-oxamide (2.5 g) is suspended in 150 ml dichloromethane. 1M Boron tribromide in dichloromethane (30 ml) is added with dry ice/acetone cooling and the solution then allowed to stir at ambient for 18 hours. Decantation into ice followed by separation of layers and reextraction with dichloromethane gives a solution which is dried, filtered, and stripped, yielding crude product. Crystallization from toluene affords N-[3,5-dimethyl-4-(4'-hydroxy-3'-isopropylphenoxy)phenyl]-oxamide, m.p. 112°–42°.

EXAMPLE 5

3,5-Dichloro-4-(3'-isopropyl-4'-methoxyphenoxy)-nitrobenzene (2.0 g) and 200 mg. of 10% platinum on carbon in 100 ml. of ethanol are hydrogenated on a Parr shaker. Catalyst is then removed by filtration through Celite and the filtrate is stripped to afford 3,5-dichloro-4-(3'-isopropyl-4'-methoxyphenoxy)-aniline. To this is added 30 g of dimethyl oxalate and this is stirred at 120° for 4 hours. Excess oxalate is removed under high vacuum from a hot water bath and the residue is chromatographed on silica gel with 9:1 toluene:ethyl acetate affording methyl N-[3,5-dichloro-4-(4'-methoxy-3'-isopropylphenoxy)-phenyl]oxamate; NMR(CDCl$_3$): δ1.2 (6H, d), 3.3 (1H,m), 3.8 (3H, s), 4.0 (3H,s), 6.5 (1H,d of d), 6.7 (1H,d), 6.8 (1H,d), 7.7 (2H,s).

The starting material is prepared as follows:

To 31 g of 2,6-dichlorophenol in 120 ml acetic acid cooled in an ice bath is added over 5 minutes 50 ml of 70% nitric acid. After stirring an hour at room temperature, the mixture is purged with nitrogen, then poured into water, filtered; the product is washed with water and dried in vacuo to give 2,6-dichloro-4-nitrophenol. NMR (CD$_3$OD): δ8.2(s).

Bis-(3-lsopropyl-4-methoxyphenyl)iodonium tetrafluoroborate (38.3 g) and 6.33 g of copper bronze are stirred in 150 ml dichloromethane and cooled in an ice water bath. A solution of 10.37 g of 2,6-dichloro-4-nitrophenol and 5.5 g of triethylamine is added dropwise. The mixture is stirred in the dark at room temperature for three days, then filtered through Celite to remove copper. The filtrate is stripped and the residue chromatographed on silica gel with 97:3 to 95:5 hexane-ethylacetate as eluent to give 3,5-dichloro-4-(3'-isopropyl-4'-methoxyphenoxy) -nitrobenzene, m.p. 75°–7°.

EXAMPLE 6

To 16.21 g of methyl N-[3,5-dichloro-4-(4'-methoxy-3'-isopropylphenoxy)-phenyl]oxamate in 400 ml dichloromethane cooled in dry ice/acetone is added 79 ml of 1M boron tribromide in dichloromethane. The bath is removed and after stirring overnight the mixture is poured into ice. After melting of the ice, the byers are separated and the aqueous phase is twice extracted with ethyl acetate. The combined organic phases are dried, filtered, and stripped to give crude acid. Reesterification is effected by dissolving in 150 ml dimethylformamide, cooling in an ice bath, and treating with 12.81 g. of cesium carbonate and 3.8 ml. of dimethyl surface. After stirring at ambient overnight, the mixture is decanted into ethyl acetate and extracted six times with brine. The organic phase is dried, filtered, and stripped, and the residue chromatographed on silica gel with 90:10 to 50:50 toluene-ethyl acetate to give methyl N-[3,5-dichloro-4-(4'-hydroxy-3'-isopropylphenoxy)-phenyl]oxamate. This is taken up in 100 ml methanol, treated with 55 ml of 1N sodium hydroxide solution, refluxed 30 minutes, and cooled to room temperature. Solvent is stripped, the residue taken up in water, and extracted twice with ether. The aqueous phase is cooled in an ice bath, acidified with concentrated hydrochloric acid, and extracted with ethyl acetate; the extract is then dried, filtered, and stripped to give crude product. Crystallization from toluene affords N-[3,5-dichloro-4-(4'-hydroxy-3'-isopropylphenoxy)-phenyl]-oxamic acid, m.p. 180°–2° dec.

EXAMPLE 7

3,5-Dimethyl-4(-3'-isopropyl-4'-methoxyphenoxy)-aniline (2.6 g), 2.48 g of (±)-ethyl 2-methanesulfonyloxy-3-phenylpropionate, and 1.18 g of diisopropyl-ethylamine in 25 ml dimethylformamide are heated at 140° for 16 hours. Solvent is removed under high vacuum and the residue dissolved in ethyl acetate and extracted with water and brine. The ethyl acetate is dried, filtered, and stripped to give an oil. Chromatography on silica gel with 9:1 to 8:2 hexane:ethyl acetate affords (±)-ethyl N-[3,5-dimethyl-4-(3'-isopropyl-4'-methoxyphenoxy)phenyl]2-amino-3-phenylpropionate. NMR(CDCl$_3$): δ1.2 (6H,d), 1.3 (3H,t), 2.0 (6H, s), 3.1 (2H,m), 3.2 (1H,m), 3.7 (3H,s), 4.0 (1H,br), 4.1 (2H,d of q), 4.3 (1H, br), 6.3 (2H,s), 6.3 (1H, d of d), 6.6 (1H,d), 6.7 (1H,d), 7.3 (5H,m).

The starting material is prepared as follows:

(±)-Phenyllactic acid (4.96 g) and ½ ml concentrated sulfuric acid in 150 ml absolute ethanol is refluxed for 18 hours. Solvent is stripped, the residue is dissolved in ether, and extracted with saturated sodium bicarbonate solution. The ether is dried, filtered, and stripped to leave (±)-ethyl phenyllactate. NMR (CDCl$_3$): δ1.3 (t, 3H), 3.0 (d of d, 1H), 3.1 (d of d, 1H), 4.2 (q, 2H), 4.4 (d of d, 1H), 7.3 (m, 5H).

(±)-Ethyl phenyllactate (11.45 g) in 20 ml pyridine is stirred in an ice bath, and 5.0 ml of methanesulfonyl chloride is added dropwise; the resulting mixture is stirred four hours with cooling, then poured into a slurry of ice and 50 ml concentrated hydrochloric acid. The precipitated solid is dissolved in ether and the ether is dried, filtered and stripped to afford a solid which is triturated with hexane to afford (±)-ethyl 2-methanesulfonyloxy-3-phenylpropionate.

EXAMPLE 8

(a) 3,5-Dichloro-4-(3'-isopropyl-4'-methoxyphenoxy)-aniline (1.83 g). 1.17 g of (±)-ethyl 2-bromopropionate, and 830 mg of diisopropylethylamine Ire heated at 140° for 16 hours. Solvent is removed with high vacuum and the residue taken up in ethyl acetate and extracted twice with water. The ethyl acetate is dried, filtered and stripped to give crude product. Chromatography on silica gel with 90:10 to 80:20 hexane:ethyl acetate as eluent affords (±)-ethyl N-[3,5-dichloro-4-(3'-isopropyl-4'-methoxyphenoxy)-phenyl]-2-aminopropionate. NMR (CDCl$_3$): δ1.2 (6H,d), 1.3 (3H,t), 1.5 (3H,d), 3.3 (1H,m), 3.8 (3H,s), 4.1 (1H,d of q), 4.3 (2H, d of q), 6.5 (1H,d of d), 6.6 (2H, s), 6.7 (1H,d), 6.9 (1H, d).

(b) Similarly prepared is ethyl N-[3,5-dichloro-4-(3'-isopropyl-4'-methoxyphenoxy)phenyl]-2-aminoacetate;

(c) Similarly prepared is ethyl N-[3,5-dimethyl-4-(3'-isopropyl-4'-methoxyphenoxy)phenyl]-2-aminopropionate;

(d) Similarly prepared is ethyl N-[3,5-dimethyl-4-(3'-isopropyl,4'-methoxyphenoxy)phenyl]-2-aminoacetate.

EXAMPLE 9

(a) To 3.08 g of (±)-ethyl N-[3,5-dimethyl-4-(3'-isopropyl-4'-methoxyphenoxy)phenyl]-2-aminopropionate in 50 ml dichloromethane cooled in dry ice/acetone is added 16 ml of 1M boron tribromide in dichloromethane. The cooling bath is removed, and after stirring 18 hours, the mixture is poured into ice. The layers are separated and the aqueous phase is twice extracted with ethyl acetate. The combined organic layers are dried, filtered, and stripped. The resulting crude oil is dissolved in 20 ml dimethylformamide, treated with 2.60 g cesium carbonate and .76 ml dimethyl sulfate, and the mixture is stirred at ambient temperature for 18 hours. The mixture is poured into ethyl acetate and extracted twice with water and four times with brine. The ethyl acetate is dried and stripped, and the remaining oil purified by chromatography on silica gel with 75:25 hexane:ethyl acetate as eluent to afford (±)-methyl N-[3,5-dimethyl4-(4'-hydroxy-3'-isopropylphenoxy)-phenyl]-2-aminopropionate. This material is taken up in 25 ml methanol, treated with 4.2 ml of 1N sodium hydroxide, and refluxed for ½ hour. The solvent is stripped and the residue redissolved in water and extracted twice with ether. The aqueous phase is acidified with glacial acetic acid and extracted twice with ethyl acetate. The ethyl acetate is dried, filtered, and stripped, and the residue purified by chromatography on silica gel with 90:10 dichloromethane:ethanol as eluent to afford (±)-N-[3,5-dimethyl-4-(4'-hydroxy-3'-isopropylphenoxy)-phenyl]-2-aminopropionic acid. NMR(CD$_3$OD): δ1.2 (6H,d), 1.5 (3H,d), 2.0 (6H, s), 3.2 (1H,m), 4.0 (1H,q), 6.3 (1H,d of d), 6.4 (2H,s), 6.6 (2H,m).

EXAMPLE 10

Ethyl N-[3,5-dichloro-4-(3'-isopropyl-4'-t-butyldimethylsiloxyphenoxy)-phenyl]aminoacetate (6.69 g) and 26 ml of 1M tetrabutylammonium fluoride in tetrahydrofuran in 25 ml tetrahydrofuran are stirred at ambient overnight. Solvent is stripped and the residue partitioned between ethyl acetate and saturated aqueous ammonium chloride. The organic phase is dried, filtered, and stripped and the residue chromatographed on silica gel with 95:5 toluene:ethyl acetate as eluent to produce ethyl N-[3,5-dichloro-4-(3'-isopropyl-4'-hydroxyphenoxy) -phenyl]aminoacetate. NMR(CDCl$_3$): δ1.2 (6H,d), 1.3 (3H,t), 3.2 (1H,m), 3.9 (2H,d), 4.3 (2H,q), 4.4 (1H,t), 4.5 (1H,s), 6.4 (1H,d of d), 6.6 (1H, d), 6.8 (1H,d).

The starting material is prepared as follows:

3,5-Dichloro-4-(3'-isopropyl-4'-methoxyphenoxy)-nitrobenzene ( 10.63 g) in 100 ml. dichloromethane is cooled in a dry ice/acetone bath and 60 ml of 1M boron tribromide in dichloromethane is added at less than −40°. After addition is completed, the mixture is stirred 18 hours at room temperature, poured into ice, and extracted twice with ethyl acetate. The combined organic layers are dried, filtered, and stripped to yield 3,5-dichloro-4-(3'-isopropyl-4' -hydroxyphenoxy)-nitrobenzene. NMR(CDCl$_3$): δ1.2 (6H,d), 3.3 (1H,m), 6.5 (1H, d of d), 6.7 (1H,d), 6.8 (1H,d), 8.3 (2H,s).

3,5-Dichloro-4-(3'-isopropyl-4'-hydroxyphenoxy)-nitrobenzene (10.2 g), 6.75 g. of t-butyldimethylsilyl chloride, 4.06 g of imidazole, and 2 mg of N,N-dimethylaminopyridine in 10 ml dimethylformamide are stirred 18 hours at room temperature. The solution is poured into ether and extracted six times with water. The ether is dried, filtered and stripped to afford 3,5-dichloro-4-(3'-isopropyl-4'-t-butyldimethylsiloxyphenoxy)-nitrobenzene. NMR (CDCl$_3$): δ0.2 (6H, s), 1.1 (9H,s), 1.2 (6H,d), 3.3 (1H,m), 6.5 (1H,d of d), 6.7 (1H,d), 8.3 (2H,s).

3,5-Dichloro-4-(3'-isopropyl-4'-t-butyldimethylsiloxyphenoxy)-nitrobenzene and 1.15 g of 10% platinum on carbon in 200 ml of ethanol is hydrogenated on a Parr shaker. Catalyst is removed by tinting through Celite and the filtrate stripped to afford 3,5-dichloro4-(3'-isopropyl-4'-t-butyldimethylsiloxyphenoxy)-aniline. This is dissolved with 3.08 ml of ethyl bromoacetate and 3.43 g of diisopropylethylamine in 50 ml dimethylformamide and heated at 140° for 18 hours. Solvent is removed with high vacuum and the residue taken up in ethyl acetate and extracted twice with water. The ethyl acetate is dried, filtered and stripped to give crude product. Chromatography on silica gel with 85:15 to 80:20 hexane:ethyl acetate as eluent affords ethyl N-[3,5-dichloro-4-(3'-isopropyl-4'-t-butyldimethylsiloxyphenoxy)phenyl]aminoacetate. NMR (CDCl₃): δ0.2 (6H,s), 1.0 (9H,s), 1.2 (6H,d), 1.3 (3H,t), 3.3 (1H,m), 3.9 (2H,d), 4.3 (2H,q), 4.4 (1H,t), 6.4 (1H,d of d), 6.6 (2H,s), 6.6 (1H,d), 6.9 (1H,d).

EXAMPLE 11

Ethyl N-[3,5-dichloro-4-(3'-isopropyl-4'-hydroxyphenoxy)-phenyl]aminoacetate (4.0 g) and 30 ml of 1N sodium hydroxide in 100 ml methanol are refluxed ½ hour and cooled to ambient. Solvent is stripped, the residue taken up in water, the solution extracted twice with ether, and the aqueous phase cooled in ice and acidified with glacial acetic acid. The resulting mixture is extracted with ethyl acetate and the ethyl acetate extract is dried, filtered and stripped. The residue is crystallized from toluene to yield N-[3,5-dichloro-4-(3'-isopropyl-4'-hydroxyphenoxy)-phenyl]-aminoacetic acid, m.p. 181°-5° (dec.).

EXAMPLE 12

3,5-Dimethyl-4-(3'-isopropyl-4'-methoxyphenoxy)-aniline (1.0 g), 730 mg of (±)-ethyl 2-bromopropionate, and 520 mg of diisopropylethylamine in 10 ml dimethylformamide are heated at 140° for sixteen hours. Solvent is removed under high vacuum and the residue is taken up in ethyl acetate and extracted twice with water. The solvent is dried, filtered, and stripped and the residue is chromatographed on silica gel 90:10 to 80:20 hexane:ethyl acetate to afford (±)-ethyl N-[3,5-dimethyl-4-(3'-isopropyl-4'-methoxyphenoxy)-phenyl]-2-aminopropionate. NMR (CDCl₃): δ1.2 (6H,d); 1.3 (3H, t), 1.5 (3H,d), 3.3 (1H,m), 3.8 (3H, s), 4.0 (1H, br.s), 4.1 (2H,q), 4.2 (1H,d of q), 6.3 (2H,s), 6.3 (1H, d of d), 6.7 (1H,d), 6.8 (1H,d).

EXAMPLE 13

Similarly prepared to procedures described in the previous examples are:

(a) N-[3,5-dimethyl-4-(3'-isopropyl-4'-hydroxyphenoxy)-phenyl]-2-aminopropionic acid.
(b) N-[3,5-dimethyl-4-(3'-isopropyl-4'-hydroxyphenoxy)-phenyl]-2-aminoacetic acid, m.p. 178°-180°.
(c) N-[3,5-dibromo-4-(3'-isopropyl-4'-hydroxyphenoxy)-phenyl]-2-aminoacetic acid, m.p. 191°-193°.
(d) N-[3,5-diiodo-4-(3'-isopropyl-4'-hydroxyphenoxy)-phenyl]-2-aminoacetic acid, m.p. 205°-207°.
(e) N-[3,5-dibromo-4-(3'-isopropyl-4'-hydroxyphenoxy)-phenyl]-2-aminopropionic acid. m.p. 85°-103° dec.
(f) N-[3,5-dibromo-4-(3'-isopropyl-4'-hydroxyphenoxy)-phenyl]-oxamic acid, m.p. 192°-194° dec.
(g) N-[3,5-diiodo-4-(3'-isopropyl-4'-hydroxyphenoxy)-phenyl]-oxamic acid, m.p. 201°-204° dec.
(h) N-[4-(3'-isopropyl-4'-hydroxyphenoxy)-phenyl]-oxamic acid, m.p. 105°-110° dec.
(i) N-[3,5-dibromo-4-(3'-isopropyl-4'-hydroxyphenoxy)-phenyl]-oxamide, m.p. 86°-90°.
(j) N-[3,5-diisopropyl-4-(3'-isopropyl-4'-hydroxyphenoxy)-phenyl]-oxamic acid, m.p. 72°-90°.
(k) N-[3,5-dimethyl-4-(4'-hydroxyphenoxy)-phenyl]-oxamic acid, m.p. 199°-200°.
(l) N-[3,5-dimethyl-4-(3'-ethyl-4'-hydroxyphenoxy)-phenyl]-oxamic acid, m.p. 177°-178° dec.
(m) N-[3-methyl-4-(3'-isopropyl-4'-hydroxyphenoxy)-phenyl]-oxamic acid, m.p. 133°-137°.
(n) N-[3,5-dimethyl-4-(3'-isopropyl-4'-hydroxyphenoxy)-phenyl]-N-methyloxamic acid, m.p. 140°-156° dec.

The starting material is prepared as follows:

3,5-Dimethyl-4-(3'-isopropyl-4'-methoxyphenoxy)-aniline (2.57g) and 1.73 ml of diisopropylethylamine in 30 ml of dry THF cooled in an ice bath are treated with 0.95 ml of ethyl chloroformate. After stirring at room temperature for 18 hours the mixture is stripped, then dissolved in ethyl acetate and extracted with water. The organic phase is dried, filtered, and stripped to give a crude oil. Chromatography on silica gel with 9:1 hexane:ethyl acetate gives ethyl N-[3,5-dimethyl-4-(4'-methoxy-3'-isopropylphenoxy)-phenyl]carbamate. NMR (CDCl₃): δ1.0 (6H,d), 1.2 (3H,t), 2.0 (6H,s), 3.3 (1H,m), 3.7 (3H, s), 4.2 (2H,q), 6.3 (1H,d of d), 6.6 (1H,d), 6.7 (1H,d), 7.1 (2H, s).

To 650 mg of lithium aluminum hydride suspended in 100 ml dry tetrahydrofuran cooled in an ice bath is added dropwise a solution of 3.06 g of ethyl N-[3,5-dimethyl-4-(4'-methoxy-3'-isopropylphenoxy)-phenyl]-carbamate in 20 ml. dry tetrahydrofuran. The mixture is refluxed three hours, then cooled in an ice bath and heated with 0.65 ml water, 0.65 ml 15% sodium hydroxide, and 1.95 ml water. The precipitate is filtered off, washed with tetrahydrofuran, and the filtrate concentrated. Chromatography on silica gel with toluene to 95:5 toluene:ethyl acetate affords N-methyl-3,5-dimethyl-4-(3'-isopropyl-4'-methoxyphenoxy)-aniline. NMR (CDCl₃): δ1.2 (6H,d), 2.1 (6H, s), 2.8 OH,s), 3.3 (1H,m), 3.8 (3H,s), 6.4 (3H,m), 6.7 (1H,d), 6.8 (1H,d).

(o) N-[3,5-diiodo-4-(4'-hydroxyphenoxy)-phenyl]-oxamic acid;
(p) N-[3,5-dichloro-4-(4'-hydroxyphenoxy)-phenyl]-oxamic acid;
(q) N-[3,5-difluoro-4-(3'-isopropyl-4'-hydroxyphenoxy)-phenyl]-oxamic acid; m.p. 160°-162°.
(r) N-[3-methyl-4-(3'-isopropyl-4'-hydroxyphenoxy)-phenyl]-oxamic acid, m.p. 133°-137°.

The intermediate, 2-methyl-4-nitrophenol, is prepared as follows:

2-Methylanisole (20 g) in 500 ml dichloromethane chilled in an ice bath is treated with 27.2 g of nitronium tetrafluoroborate and stirred two days. The mixture is poured into water, the layers are separated, and the aqueous phase is washed with dichloromethane. The combined organic layers are dried, filtered, stripped, and chromatographed on silica gel with 9:1 to 8:2 hexane:ethyl acetate to give 2-methyl-4-nitroanisole. NMR (CDCl₃): δ2.3 (3H,s), 3.9 (3H,s), 6.9 (1H,d), 8.0 (1H,d), 8.1 (1H,d of d).

2-Methyl-4-nitroanisole (4.0 g) in 50 ml 1:1 hydrobromic acid:acetic acid is heated 12 hours at 120°. Solvent is stripped, the residue taken up in water and ethyl acetate, the mixture is filtered to remove insolubles, and the layers are separated. The organic phase is dried, filtered, and stripped to afford 2-methyl-4-nitrophenol. NMR (CDCl₃): δ2.3 (3H,s), 6.8 (1H,d), 7.9 (1H,d of d), 8.0 (1H,d).

EXAMPLE 14

N-[3,5-Dibromo-4-(4'-hydroxy-3'-isopropylphenoxy)-phenyl]oxamic acid (500 mg) and 290 mg of 2-ethoxy-1-ethoxycarbonyl-1,2-dihydroquinoline are dissolved in 20 ml. of dimethylformamide. The solution is saturated with methylamine gas, capped, and stirred at ambient for three days. Solvent is removed under high vacuum and the residue chromatographed on silica gel with 95:5 toluene:ethyl acetate to 75:25 ethyl acetate:ethanol to afford N-[3,5-dibromo-4-(4'-hydroxy-3'-isopropylphenoxy)-phenyl]-N'-methyloxamide, m.p. 140°-5°.

EXAMPLE 15

Methyl N-[3,5-dimethyl-4-(4'-methoxy-3'-isopropylphenoxy)phenyl]oxamate (2.02 g) in 50 ml methanol is treated with 6.0 ml of 1.0 N sodium hydroxide, refluxed ½ hour, and cooled to ambient. Solvent is evaporated, the residue dissolved in water, extracted with ether, and the aqueous phase neutralized with 6 ml of 1.0 N hydrochloric acid. The resulting precipitate is washed with water, taken up in ethyl acetate and ethanol and the solution dried, filtered, and stripped to leave crude product which is crystallized from toluene to afford N-[3,5-dimethyl4-(4'-methoxy-3-isopropylphenoxy)-phenyl]oxamic acid, m.p. 179°-83°(dec.).

EXAMPLE 16

(a) N-[3,5-Dimethyl-4-(4'-hydroxy-3'-isopropylphenoxy)-phenyl]oxamic acid (8.48 g), 8.04 g of cesium carbonate, and 2.4 ml of dimethyl surface are stirred overnight in 50 ml dimethylformamide. The mixture is poured into ethyl acetate and extracted once with water and five times with brime. The organic layer is dried, filtered, and stripped to afford an oil which is chromatographed on silica gel with from 90:10 to 50:50 toluene-:ethyl acetate to give purified material which is then crystallized from toluene to afford methyl N-[3,5-dimethyl-4-(4'-hydroxy-3'-isopropylphenoxy)-phenyl]oxamate, m.p. 190°-3°.

(b) N-[3,5-Dichloro-4-(4'-hydroxy-3'-isopropylphenoxy)-phenyl]oxamic acid (9.59 g), 8.13 g of cesium carbonate, and 2.4 ml of dimethyl sulfate are stirred overnight in 50 ml dimethylformamide. The mixture is poured into ethyl acetate and extracted once with water and five times with brime. The organic layer is dried, filtered, and stripped and the residue chromatographed on silica gel with from 90:10 to 50:50 toluene:ethyl acetate to yield desired product which is crystallized from toluene to produce methyl N-[3,5-dichloro-4-(4'-hydroxy-3'-isopropylphenoxy) -phenyl]oxamate, m.p. 181°-5°.

EXAMPLE 17

N-[3,5-Dichloro-4-(4'-hydroxy-3'-isopropylphenoxy)-phenyl]oxamic acid (3.0 g), 2.55 g of cesium carbanate and 0.93 ml of benzyl bromide are stirred in 20 ml dimethylformamide overnight The mixture is poured into ethyl acetate and extracted with water once and brine five times. The organic layer is dried, filtered, and stripped and the residue chromatographed on silica gel with 9:1 toluene:ethyl acetate as eluent to give product Crystallization from toluene yields benzyl N-[3,5-dichloro-4-(4'-hydroxy-3'-isopropylphenoxy)-phenyl]oxamate, m.p. 164°-6°.

EXAMPLE 18

To 100 mg of N-[3,5-dimethyl-4-(4'-hydroxyphenoxy)-phenyl]oxamic acid in 20 ml ammonium hydroxide cooled in an ice bath is added 6.06 ml of 0.066M ethanolic bromine. After overnight stirring the solution is concentrated slightly and acidified with 2N hydrochloric acid. The solid is filtered off and recycled as above three more times. The final crude solid is crystallized from toluene to afford N-[3,5-dimethyl-4-(4'-hydroxy-3'-bromophenoxy)-phenyl]oxamic acid, m.p. 161°-5° (dec.)

EXAMPLE 19

To 250 mg of N-[3,5-dichloro-4-(4'-hydroxyphenoxy)-phenyl]oxamic acid in 20 ml ammonium hydroxide cooled in an ice bath is added 2.2 ml of 0.394M ethanolic iodine. When addition is complete, the solution is stirred at ambient for two hours, then concentrated slightly and filtered. The filtrate is acidified with 2N hydrochloric acid and twice extracted with ethyl acetate. The organic fractions are combined, dried, filtered, and stripped to give a solid which is crystallized from toluene to afford N-[3,5-dichloro-4-(4'-hydroxy-3'-iodophenoxy)phenyl]oxamic acid, m.p. 218°-20° (dec.)

EXAMPLE 20

Methyl N-[3,5-dimethyl-4-(4'-hydroxy-3'-isopropylphenoxy)-phenyl]-oxamate (1.74 g), 50 ml of dihydropyran, 1 ml dimethylformamide, and 3 drops of concentrated hydrochloric acid are stirred at room temperature overnight. Solvent is evaporated and the residue chromatographed on silica gel with 9:1 through 8:2 toluene:ethyl acetate as eluent to yield methyl N-{3,5-dimethyl-4-[3'-isopropyl-4'-(2''-tetrahydropyranyloxy)-phenoxy]phenyl}-oxamate. NMR (CD$_3$OD): $\delta$1.2 (6H, d of d), 1.7 (6H,m), 2.1 (6H, s) 3.3 (1H,m), 3.5 (2H,m), 3.9(3H, s), 5.3 (1H,t), 6.4 (1H, d of d), 6.7 (1H, d), 7.0 (1H, d), 7.5 (2H,s)

EXAMPLE 21

Methyl N-[3,5-dimethyl-4-(3'-isopropyl-4'-(2''-tetrahydropyranyloxy)-phenoxy)phenyl]oxamate (1.23 g) and 3.1 ml of 1.0N sodium hydroxide in 40 ml methanol are refluxed 30 min., then stirred at ambient temperature overnight. Solvent is evaporated, the residue dissolved in water, extracted with ether, chilled in an ice bath and neutralized with 3.1 ml 1.0N hydrochloric acid. The mixture is extracted twice with ethyl acetate and the combined organic fractions dried, filtered, and stripped, giving N-[3,5-dimethyl-4-(3'-isopropyl-4'-(2''-tetra hydropyranyloxy)-phenoxy)-phenyl]oxamic acid, m.p. 152°-6° (dec.)

EXAMPLE 22

Cholic acid (1.71 g), 1.50 g of methyl N-[3,5-dimethyl-4-(4'-hydroxy-3'-isopropylphenoxy)-phenyl ]oxamate, 1.61 g of N-(dimethylaminopropyl)-N'-ethylcarbodiimide hydrochloride, and 260 mg of N,N-dimethylaminopyridine are stirred in 150 ml tetrahydrofuran for 48 hours. Solvent is evaporated and the residue is redissolved in ethyl acetate and is washed with water then brine. Solvent is dried, filtered and stripped, and the residue is chromatographed on silica gel with ethyl acetate/ethanol to afford 4-{2,6-dimethyl-4-[(2-methoxy-1,2-dioxoethyl)amino]phenoxy}-2-isopropylphenyl 3,7,12(3$\alpha$,5$\beta$,7$\alpha$, 12$\alpha$)-trihydroxycholan-24-oate.

EXAMPLE 23

Cholic acid (1.79 g), 2.08 g of benzyl N-[3,5-dichloro-4-(4'-hydroxy-3'-isopropylphenoxy)-phenyl ]oxamate, 1.68 g of N-(dimethylaminopropyl)-N'-ethylcarbodiimide hydrochloride and 270 mg of dimethylaminopyridine are stirred in 150 ml tetrahydrofuran for 18 hours. Solvent is evaporated and the residue is redissolved in ethyl acetate and extracted with water. The ethyl acetate is dried, filtered, and stripped and the residue chromatographed on silica gel with 20:80 through 10:90 toluene:ethyl acetate to afford 4-{4-[(2-benzyloxy-1,2-dioxoethyl) amino]-2,6-dichlorophenoxy}-2-isopropylphenyl 3,7,12(3α,5β,7α, 12α)-trihydroxycholan-24-oate, as an amorphous solid, m.p. 119°–128° dec.

EXAMPLE 24

4-{4-[(2-benzyloxy-1,2-dioxoethyl)amino]-2,6-dichlorophenoxy}-2-isopropylphenyl 3,7,12(3α,5β,7α, 12α)-trihydroxycholan-24-oate (260 rag) and 26 mg of 10% palladium on carbon in 50 ml ethanol are treated with hydrogen on a Parr shaker. Catalyst is removed by filtering through Celite and the filtrate is stripped to give 4-{2,6-dichloro-4-[(2-hydroxy-1,2-dioxoethyl) amino]phenoxy}-2-isopropylphenyl 3,7, 12(3α,5β,7α, 12α)-trihydroxycholan-24-oate, as an amorphane monohydrate, m.p. 180°–92° (dec.).

EXAMPLE 25

3,5-Dibromo-4-(3'-isopropyl-4'-methoxyphenoxy)-thiophenol (760 mg), 0.22 ml of ethyl bromoacetate, and 260 mg of diisopropylethylamine in 10 ml dimethylformamide are heated sixteen hours at 140°. Solvent is removed under vacuum, the residue dissolved in ethyl acetate and extracted twice with water. The ethyl acetate is dried, filtered, and stripped to give crude product. Chromatography on 75 g silica gel with 9:1 hexane-ethylacetate as eluent affords ethyl S-[3,5-dibromo-4-(3'-isopropyl-4'-methoxyphenoxy)-phenyl]-2-mercaptoacetate. NMR (CDCl$_3$): δ1.1 (6H,d), 1.3 (3H,t), 3.3 (1H,m), 3.7 (2H, s), 3.8 (3H,s), 4.2 (2H,q), 6.4 (1H,d of d), 6.7 (1H,d), 6.8 (1H,d), 7.6 (2H, s).

The starting material is prepared as follows:

3,5-Dibromo-4-(3'-isopropyl-4'-methoxyphenoxy)-aniline (1.87 g), prepared according to e.g. procedure illustrated in example 1 ) in 40 ml of 1:1 dimethylsulfoxide: conc. hydrochloric acid is chilled in an ice bath and added dropwise to 340 mg of sodium nitrite. After stirring cold for 20 minutes the mixture is transferred portionwise to 1.44 g of potassium ethyl xanthate in 2 ml water over 15 minutes and the resulting mixture stirred at 45° for 18 hours. The resulting dark mixture is poured into ethyl acetate and extracted with water once and brine five times. The ethyl acetate is dried, filtered, and stripped to afford a dark oil. Chromatography on 250 g of silica gel with 97:3 hexane: ethyl acetate as eluent gives ethyl S-[3,5-dibromo-4-(3'-isopropyl-4'-methoxyphenoxy)-phenyl]xanthate. NMR (CDCl$_3$): δ1,1 (6H,d), 1.4 (3H, t), 3.3 (1H,m), 3.7 (3H,s), 4.7 (2H,q), 6.4 (1H, d of d), 6.7 (1H,d), 6.8 (1H,d), 7.7 (2H,s).

Ethyl S-[3,5-dibromo-4-(3'-isopropyl-4'-methoxyphenoxy)-phenyl]xanthate (630 mg) in 12 ml ethanol is treated with 99.6 mg of potassium hydroxide in 2 ml of water and the solution refluxed three hours. The solvent is removed and the residue redissolved in water and acidified with concentrated hydrochloric acid. The mixture is extracted with ethyl acetate and the organic phase dried, filtered and stripped to afford 3,5-dibromo-4-(3'-isopropyl-4'-methoxyphenoxy) -thiophenol.NMR (CDCl$_3$): δ1.1 (6H,d), 3.3 (1H,m), 3.7 (1H,s), 6.4 (1H,d of d), 6.7 (1H,d), 6.8 (1H,d), 7.7 (2H,s).

EXAMPLE 26

Ethyl S-[3,5-dibromo-4-(3'-isopropyl-4'-methoxyphenoxy)-phenyl]-2-mercaptoacetate (450 mg) in 25 ml dichloromethane is cooled in a dry ice/acetone bath and treated dropwise with 1.8 ml of 1M boron tribomide in dichloromethane. When addition is complete, the mixture is stirred at ambient for 18 hours, then poured into ice. The layers are separated, the aqueous phase extracted with ethyl acetate, and the combined organic phase dried, filtered, and stripped. The residual oil is taken up in aqueous base, the solution is washed twice with ether, then acidified with concentrated hydrochloric acid and extracted with ethyl acetate. The ethyl acetate is dried, filtered, and stripped to afford S-[3,5-dibromo-4-(3'-isopropyl-4'-hydroxyphenoxy) -phenyl]-2-mercaptoacetic acid. NMR (CDCl$_3$): δ1.2 (6H,d), 3.2 (1H,m), 3.7 (2H,s), 6.3 (1H,d of d), 6.6 (2H,m), 7.7 (2H, s).

EXAMPLE 27

A solution of 480 mg (137 mmol) of [5-(4-amino-2,6-dimethylphenoxy)-2-hydroxyphenyl](4-fluorophenyl)-methanone in 5 ml of diethyl oxalate is heated at 100° for 2.5 hours. The excess diethyl oxalate is evaporated with a nitrogen stream and the residue is triturated with petroleum ether and filtered. The solid is dissolved in methylene chloride, the solution is filtered and the filtrate is evaporated to give ethyl N-[4-[3'-(4-fluorobenzoyl)4'-hydroxyphenoxy]-3,5-dimethylphenyl]oxamate.

The starting material is prepared as follows:

To a solution of 26.0g (61.0 mmol) of 4,4'-methoxydiphenyliodonium tetrafluoroborate and 10.7 g (64.0 mmol) of 2,6-dimethyl-4-nitrophenol in 250 ml methylene chloride is added 0.5 g of copper powder and 10 ml (72.0 mmol) of triethylamine. The reaction mixture is stirred at room temperature for 6 days, then filtered. The filtrate is washed with 100 ml of 1N hydrochloric acid, 100 ml of water, dried (CaSO$_4$), filtered and evaporated. The residue is washed with ethanol to give 3,5-dimethyl-4-(4'-methoxyphenoxy)-nitrobenzene, m.p. 117°–20°.

To a solution of 4.5 g (16.5 mmol) of 3,5-dimethyl-4-(4'-methoxyphenoxy)nitrobenzene and 6.63 g (41.8 mmol) of p-fluorobenzoyl chloride in 100 ml methylene chloride is added 15.8 g (83.3 mmol) of titanium trichloride. The reaction mixture is stirred for 8 days at room temperature, then poured into ice water (300 ml) and stirred 2 hours. The organic layer is separated, washed with 5% aqueous sodium carbonate, water, dried (CaSO$_4$) and evaporated. The residue is triturated with ether-petroleum ether and recrystallized from methanol to give (4-fluorophenyl)[2-methoxy-5-(2,6-dimethyl-4-nitrophenoxy)phenyl]-methanone, m.p. 167°–168°.

A solution of 5.12 g (13.0 mmol) of (4-fluorophenyl)[2-methoxy-5-(2,6-dimethyl-4nitrophenoxy) phenyl]methanone in 100 ml methylene chloride is chilled in an ice bath and 40 ml (40 mmol) of 1.0 M boron trichloride in methylene chloride is gradually added. The solution is stirred at room temperature overnight, then poured into 300 ml of ice water and stirred 2 hours. The organic layer is separated, washed with 5% aqueous sodium carbonate, water, dried (CaSO$_4$) and evaporated. The residue is recrystallized from ethanol to give (4-fluorophenyl)[2-hydroxy-5-(2,6-dimethyl-4 nitrophenoxy)phenyl]methanone, m.p. 148°–150°.

A solution of 2.77 g (7.3 mmol) of (4-fluorophenyl)[2-hydroxy-5-(2,6-dimethyl-4-nitrophenoxy) phenyl]methanone in 200 ml ethyl acetate with 1.0 g of 10% palladium on carbon is hydrogenated on a Parr apparatus for 2.5 hours at 50 psi and room temperature, then filtered and evaporated to give [5-(4-amino-2,6-dimethylphenoxy)-2-hydroxyphenyl](4-fluorophenyl)methanone.

EXAMPLE 28

A slurry of Raney nickel (10 ml) is washed with water (3×25 ml), ethanol (2×25 ml) and added to a solution of 1.4 g (3.1 mmol) of ethyl N-[4-[3'-(4-fluorobenzoyl)-4'-hydroxyphenoxy ]-3,5-dimethylphenyl]oxamate in 20 ml ethyl acetate diluted with 80 ml ethanol. The reaction mixture is hydrogenated on a Parr apparatus for 2 hours at 45 psi and room temperature, then filtered and evaporated. The residue is recrystallized from ether-petroleum ether to give ethyl N-[4-[3'-[(4-fluorophenyl) hydroxymethyl]-4'-hydroxyphenoxy]-3,5-dimethylphenyl]oxamate, m.p. 146°-148°.

EXAMPLE 29

A solution of 900 mg (2.0 mmol) of ethyl N-[4-[3'-(4-fluorobenzoyl)-4'-hydroxyphenoxy]-3,5-dimethylphenyl]oxamate in 20 ml of ethanol and 2.5 ml (2.5 mmol) of 1.0 N aqueous sodium hydroxide is refluxed 2 hours, then evaporated. The residue is dissolved in water and the aqueous solution is washed with ethyl acetate, acidified with 6 N aqueous hydrochloric acid and extracted with ether. The ether layer is washed with water, dried (CaSO$_4$) and evaporated. Recrystallization from methylene chloride—petroleum ether gives N-[4-[3'-(4-fluorobenzoyl)4'-hydroxyphenoxy]-3,5-dimethylphenyl]oxamic acid, m.p. 160°-162° dec.

EXAMPLE 30

The following compounds are prepared using essentially the same procedure as described in the above examples for N-[4-[3'-(4-fluorobenzoyl)4'-hydroxyphenoxy]-3,5-dimethylphenyl]oxamic acid, via the corresponding ethyl ester.
  (a) N-[3,5-dichloro-4-[3'-[(4-fluorobenzoyl)]4'-hydroxyphenoxy]phenyl]oxamic acid, m.p. 196°;
  (b) N-[3,5-dichloro-4-[3'-(4-chlorobenzoyl)-4'-hydroxyphenoxy]phenyl]oxamic acid, m.p. 199°;
  (c) N-[4-[3'-(4-chlorobenzoyl)-4'-hydroxyphenoxy]-3,5-dimethylphenyl]oxamic acid, m.p. 188°;
  (d) N-[3,5-dichloro-4-[4'-hydroxy-3'-(1-oxobutyl)-phenoxy]phenyl]oxamic acid, m.p. 183°;
  (e) N-[4-[3'-(benzoyl)-4'-hydroxyphenoxy]-3,5-dimethyl-phenyl]oxamic acid.

EXAMPLE 31

To a solution of 300 mg (0.71 mmol) of N-[4-[3'-(4-fluorobenzoyl)4'-hydroxyphenoxy]-3,5-dimethylphenyl]oxamic acid in 10 ml methanol is added 130 mg (3.5 mmol) of sodium borohydride. The reaction mixture is stirred at room temperature for 15 minutes, then diluted with water, acidified with 6 N aqueous hydrochloric acid and extracted with ether. The ether layer is washed with water, dried (CaSO$_4$) and evaporated. The residue is taken up in methylene chloride, filtered and evaporated. Recrystallization from methylene chloridepetroleum ether gives N-[4-[3'-[(4-fluorophenyl) hydroxymethyl]-4'-hydroxyphenoxy]-3,5dimethylphenyl]oxamic acid, m.p. 142°-147° dec.

EXAMPLE 32

The following compounds are prepared using essentially the same procedure as described above for N-[4-[3'-(4-fluorophenyl) hydroxymethyl]-4'-hydroxyphenoxy]-3,5-methylphenyl]oxamic acid.
  (a) N-[3,5-dichloro-4-[3'-[(4-chlorophenyl)hydroxymethyl]-4'-hydroxyphenoxy]phenyl]oxamic acid, m.p. 155°;
  (b) N-[4-[3'-[(4-chlorophenyl)hydroxymethyl]-4'-hydroxyphenoxy]-3,5-dimethylphenyl]oxamic acid, m.p. 123°.

EXAMPLE 33

A solution of 660 mg (1.96 mmol) of 4-(4-amino-2,6-dimethylphenoxy)-2-[(4-fluorophenyl)methyl]phenol in 5 ml diethyl oxalate is heated at 100° for 1.25 hours. The excess diethyl oxalate is evaporated with a nitrogen stream and the residue is triturated with petroleum ether and filtered. Flash chromatography gives ethyl N-[4-[3-[(4-fluorophenyl)methyl]-4'-hydroxyphenoxy]-3,5-dimethylphenyl]oxamate, m.p. 153°-156°.

The starting material is prepared as follows:

To a solution of 2.2 g (5.55 mmol) of (4-fluorophenyl)[2-methoxy-5-(2,6-dimethyl-4-nitrophenoxy)phenyl]methanone in 10 ml methylene chloride and 3 ml trifluoroacetic acid is added 2.1 g (18.0 mmol) of triethylsilane. The solution is stirred overnight at room temperature, then diluted with ether (100 ml) and washed with water, 5% aqueous sodium carbonate, water, dried (CaSO$_4$) and evaporated. The residual oil is flash chromatographed to give 1-[(4-fluorophenyl)methyl]-2-methoxy-5-(2,6-dimethyl-4-nitrophenoxy)benzene, m.p. 105°-110°.

To a solution of 1.7 g (4.5 mmol) of 1-[(4-fluorophenyl)methyl]-2-methoxy-5-(2,6-dimethyl -4-nitrophenoxy)benzene in 100 ml methylene chloride is added 13.5 ml (13.5 mmol) 1.0 N boron tribromide in methylene chloride. The solution is stirred overnight at room temperature, poured into ice water (300 ml) and stirred 1 hour. The organic layer is separated, washed with water, dried (CaSO$_4$) and evaporated. Flash chromatography of the residue gives 2-[(4-fluorophenyl)methyl]-4-(2,6-dimethyl-4-nitrophenoxy)phenol, m.p. 127°-132°.

A slurry of Raney nickel (10 ml) is washed with water (2×25 ml), ethanol (2×25 ml) and added to a solution of 2-[(4-fluorophenyl)methyl]-4-(2,6-dimethyl-4-nitrophenoxy) phenol in 100 ml ethanol. The reaction mixture is hydrogenated on a Parr apparatus for 1.5 hours at 45 psi and room temperature, filtered and evaporated. Recrystallization from ether-petroleum ether gives 4-(4-amino-2,6-dimethylphenoxy)-2-[(4-fluorophenyl)methyl]phenol, m.p. 179°-182°.

EXAMPLE 34

A solution of 440 mg (1.0 mmol) of ethyl N-[4-[3'-[(4-fluorophenyl)methyl]4'-hydroxyphenoxy]-3,5-dimethylphenyl]oxamate in 20 ml ethanol and 1.2 ml (1.2 mmol) 1.0 N aqueous sodium hydroxide is refluxed for 1 hour, then evaporated. The residue is dissolved in water, and the solution is washed with ether, acidified with 6 N aqueous hydrochloric acid and extracted with ether. The ether layer is washed with water, dried (CaSO$_4$) and evaporated. The residue is recrystallized from methylene chloride to give N-[4-[3'-(4-fluorophenyl) methyl]-4'-hydroxyphenoxyl-3,5-dimethylphenyloxamic acid, m.p. 182°-184° dec.

EXAMPLE 35

The following examples are prepared using essentially the same procedure as described above for N-[4-[3'-(4-fluorophenyl)methyl]-4'-hydroxyphenoxy]-3,5-dimethylphenyl]oxamic acid.
  (a) N-[3,5-dichloro-4-[3'-[(4-fluorophenyl)methyl]-4'-hydroxyphenoxy]phenyl]oxamic acid, m.p. 180°;

(b)  N-[3,5-dichloro-4-[3'-[(4-chlorophenyl)methyl]-4'-hydroxyphenoxy]phenyl]oxamic acid, m.p. 185°;
(c)  N-[4-[4'-hydroxy-3'-(phenylmethyl)phenoxy]-3,5-dimethylphenyl]oxamic acid, m.p. 154°;
(d)  N-[4-[3'-[(4-chlorophenyl)methyl]-4'-hydroxyphenoxy]-3,5-methylphenyl]oxamic acid, m.p. 155°.

EXAMPLE 36

3,5-Dichloro-4-[3'-(4-fluorobenzyl)4'-methoxyphenoxy]nitrobenzene (3.64 g) and 360 mg of 10% platinum on carbon in 200 ml ethanol is hydrogenated on a Parr shaker. Catalyst is removed by filtration through Celite and the filtrate stripped to afford 3,5-dichloro-4-[3'-(4-fluorobenzyl) 4'-methoxyphenoxy]-aniline. This is redissolved with 1.10 ml ethyl bromoacetate and 1.28 g of diisopropylethylamine in 30 ml dimethylformamide and heated at 140° for 18 hours. Solvent is removed with high vacuum and the residue dissolved in ethyl acetate and extracted twice with water. The ethyl acetate is dried, filtered and stripped to give crude product. Chromatography on silica gel with 80:20 to 70:30 hexane:ethyl acetate affords pure ethyl N-[3,5-dichloro-4-[3'-(4-fluorobenzyl)-4'-methoxyphenoxy]-phenyl]aminoacetate; NMR (CDCl$_3$): δ1.3 (3H, t), 3.7 (3H, s), 3.9 (2H, s), 3.9 (2H, s), 4.3 (2H,q), 6.6 (1H, d of d), 6.7 (1H, d), 6.8 (1H, d), 6.9 (2H, m), 7.1 (2H, m), 7.3 (2H, s).

EXAMPLE 37

Ethyl N-[3,5-dichloro-4-[3'-(4-fluorobenzyl)-4'-methoxyphenoxy]-phenyl]aminoacetate (2.14 g) in 25 ml dichloromethane is chilled in dry ice-acetone and 9.0 ml of 1.0M boron tribromide in dichloromethane is added dropwise. After stirring at ambient overnight the mixture is poured onto ice and extracted twice with ethyl acetate. The ethyl acetate extract is dried, filtered and snipped to give crude product which is then treated with 1.46 g cesium carbonate and 420 μl dimethyl sulfate in 20 ml dimethylformamide and stirred at room temperature overnight. The solution is poured into ethyl acetate and extracted once with water and five times with brine. The ethyl acetate is dried, filtered, and snipped and the residue chromatographed on silica gel with from 9:1 to 8:2 toluene:ethyl acetate as eluent to yield methyl N-[3,5-dichloro-4-(3'-(4-fluorobenzyl)-4'-hydroxyphenoxy]-phenyl]aminoacetate. This compound is then refluxed one half hour with 4.4 ml 1.0M sodium hydroxide in 50 ml methanol, cooled to room temperature, snipped, redissolved in water, and extracted twice with ether. The aqueous phase is chilled with ice, acidified with glacial acetic acid, filtered, and the precipitate is dissolved in ethyl acetate. The solution is dried, filtered, stripped, and the residue is crystallized from toluene to yield N-[3,5-dichloro-4-[3'-(4-fluorobenzyl)-4'-hydroxyphenoxy]-phenyl]aminoacetic acid, m.p. 197°–203°.

EXAMPLE 38

3,5-Dimethyl-4-(3'-isopropylphenoxy)-nitrobenzene (5.21 g) and 521 mg of 10% platinum on carbon in 150 ml ethanol are reduced under hydrogen on a Pan-shaker. The solution is filtered through Celite to remove catalyst and the filtrate is stripped to give 3,5-dimethyl-4-(3'-isopropylphenoxy)-aniline which is then fused with 50 g of dimethyl oxalate at 120° for four hours. The resulting mixture is concentrated under high vacuum and the residue chromatographed on silica gel with 9:1 toluene:ethyl acetate as eluent to yield methyl N-[3,5-dimethyl-4-(3'-isopropylphenoxy)-phenyl]oxamate; NMR (CDCl$_3$): δ1.2 (6H, d), 2.1 (6H, s), 2.8 (1H, m), 4.0 (3H, s), 6.5 (1H, d of d), 6.7 (1H, t), 6.9 (1H, d of d), 7.2 (1H, t), 7.4 (2H, s), 8.8 (1b, br s).

The starting material is prepared by reaction of 3-isopropyl-phenol with 4-chloro-3,5-dimethylnitrobenzene using methodology described in example 1.

EXAMPLE 39

3,5-Dimethyl-4-(3'-isopropyl-4'-hydroxyphenoxy)-aniline (1.65 kg, 6.08 mmol) is suspended in diethyl oxalate (8.5 L) and heated to an internal temperature of 100°. At 85° a complete solution is obtained. After 3 hours at 100° the reaction is complete. On cooling to 50° the solution is diluted with heptane (8 L) and the mixture is cooled to 5°. The solids are collected by filtration and the filter cake is washed with heptane (3×200 mL). After drying overnight (50°, 1 Torr) the material is dissolved in hot ethyl acetate (12 L). This solution is diluted with heptane (12 L) and the mixture is cooled to 10° for 1 hour and filtered. The filter cake is washed with heptane (2×1 L) and then dried for 72 hours (60°, 0.5 Torr) to obtain ethyl N-[3,5-dimethyl-4-(4'-hydroxy-3'-isopropylphenoxy)-phenyl]oxamate, m.p. 170°–171°.

The starting material is prepared as follows:

2-Isopropylphenol (5.0 kg, 36.7 mol) is dissolved in ethyl acetate (20.8 L) and to this is added triethylamine (4.48 kg, 44.1 mmol). This solution is cooled to -12° and to this is added acetyl chloride (3.15 kg, 40.2 tool) over a period of 2.5 hours keeping the temperature below −10°. Triethylamine hydrochloride precipitates immediately. After the addition is complete stirring is continued for 1 hour at 15° at which time a solid mass is formed. This is dissolved by the addition of water (12L). After separation of the layers the organic layer is further washed with water (233 12L) and evaporated in vacuo (50°, 2 Torr) and then at 70°, 2 Torr to give 2-isopropyl-phenyl acetate as a residual amber oil.

2-Isopropylphenyl acetate (3.24 kg, 18.2 mol) is dissolved in nitrobenzene (12.5 L). After cooling this solution to 10°, aluminum chloride (6.0 kg/45.0 mmol) is added in portions, keeping the temperature at approximately 20°. After the addition is complete the reaction mixture is heated at 35° for 18 hours. After cooling to room temperature this mixture is poured onto hydrochloric acid (1.0 N, 16.5 L), keeping the temperature between 20°-25° with ice-cooling. Stirring is continued for 15 minutes after the addition is complete. At this time the solids are collected by filtration and washed with water (20 L). This material is combined with that of a run of exactly the same size and dissolved in methanol (16l,). To this solution is added charcoal (100 g) and after stirring for 30 minutes this mixture is filtered. To this decolorized solution water (18 L) is slowly added to precipitate the product. At this time the mixture is cooled to 4° C. for 1 hour and the solids are collected by filtration, washed with hexane (4×2 L) to remove residual nitrobenzene and dried in vacuo (50° C., 1 Torr) for 18 hours to obtain 4-acetyl-2-isopropylphenol, mp 142°–144°.

4-Acetyl-2-isopropylphenol (3.69 kg, 20.7 mol) is dissovled in dimethylformamide (14 L). To this solution is then added powdered anhydrous potassium carbonate (3.16 kg, 22.8 mol), anhydrous potassium iodide (369 g, 2.22 mol) and benzyl chloride (2.88 kg, 22.8 mol). This mixture is then heated to 80° for 2 hours, cooled to 50° and diluted with water (46 L). After cooling to 5° the mixture is stirred for 1 hour and the solids are collected by filtration and washed with water (20 L). After air drying overnight, the solids are dissolved in methanol (16 L) at 50° and filtered into a 20 gallon container. The filtrate is diluted with water (10 L) over a period of 20 minutes at 40°. After the addition is complete the mixture is stirred for 1 hour at 5° and the solids are filtered and dried in vacuo (80°, 15 Torr) for 5 days to obtain 4-benzyloxy-3-isopropylacetophenone, m.p. 55°–56°.

4-Benzyloxy-3-isopropylacetophenone (5.50 kg, 20.5 mol) is dissolved in acetic acid (25 L). To this solution is added anhydrous sodium acetate (502 g, 6.10 mol) with stirring which is continued until complete solution is obtained at 20°. At this time peracetic acid (35%, 8.90 kg, 40.1 mol) is added all at once. At first the temperature drops to 14° and then a slow exotherm occurs with the temperature rising from 14°–32° over a period of 5 hours. The exotherm is controlled by a cold water bath. After stirring overnight at room temperature, the solution is cooled to 15° and a solution of sodium sulfite (4.5 kg, 35.7 mol) in water (21) L) is added slowly, keeping the temperature below 20°. When all the solution is added, a negative starch/iodide reaction is obtained. The mixture is extracted with toluene (3×10 L) and the combined extracts are washed with water (4×12 L). Distillation of the toluene in vacuo (50°, 3 Torr) gives 4-benzyloxy-3-isopropylphenyl acetate as an amber oil.

4-Benzyloxy-3-isopropylphenyl acetate (5.59 kg, 19.7 mol) is added to a solution of sodium hydroxide (1.20 kg, 30.0 mol) in a mixture of water (30 L) and methanol (30 L). This solution is stirred at 24° for 1 hour. A black-colored solution develops. This is concentrated in vacuo (40°, 3 Torr) to remove the methanol. This residue is then extracted with ethyl acetate (2×16 L) and the combined organic layers are washed with aqueous sodium hydroxide (1 N, 2×10 L) and water (3×12 L). The solvent is stripped in vacuo (50°, 3 Torr) to yield an amber oil. This oil is then trimmed with heptane (10 L) for 4 hours and the allowed to stand overnight at room temperature at which time the solids are collected by filtration and washed with cold heptane (2×1 L). After air-drying, the product is further dried in vacuo (25°, 120 Torr) for 72 hours to give 4-benzyloxy-3-isopropylphenol as a low melting solid, m.p. 39°–40°.

A suspension of 4-nitro-2,6-dimethylphenol (2.68 kg, 16.1 mol) in dichloromethane (30 L) is cooled to −15°. To this is added pyridine (3.17 kg, 19.5 mol) all at once to obtain a black solution. Tiffin anhydride (5.50 kg, 19.5 mol) is then added over a period of 2 hours, keeping the temperature between −10° and −5°After the addition is complete stirring is continued for 2.5 hours at −3°. At this time cold water (3°, 24 L) is added dissolving the black suspension. After separation of the layers the organic layer is washed with hydrochloric acid (1 N, 12 L), water (2×12 L), aqueous sodium hydroxide (2×12 L) and water (4×12 L). All the aqueous washes are kept cold (3°) and the batch temperature at this time is approximately 5°throughout. After drying over magnesium sulfate (5.0 kg), the organic layer is filtered and evaporated in vacuo at 40°. The residue is dissolved in heptane (4 L) and the dark solution is stirred and seeded to initiate crystallization. After standing overnight at 4°the solids are collected by filtration and washed with heptane (2×500 mL). After drying in vacuo (24°, 120 Torr) for 24 hours 4-nitro-2,6-dimethylphenyl trifluoromethanesulfonate is obtained as a brownish solid, m.p. 64°–66°.

4-Nitro-2,6-dimethylphenyl trifluoromethanesulfonate (4.06 kg, 13.6 mol) is dissolved in anhydrous N-methylpyrrolidinone (42 L) and to this solution is added anhydrous lithim chloride (900 g) all at once. The internal temperature is raised to 120° at which time the color changes to a dark golden brown. After 10 hours at this temperature the color of the solution is dark brown. The reaction is then cooled to 5° and diluted with cold water (5°, 21 L) at such a rate as to keep the temperature below 1:5°. After the addition is complete the mixture is stirred for 1 hour at 5°. The product is collected by filtration and washed with water (4×1 L). This dark brown solid is dissolved in t-butyl methyl ether (42 L) and stirred first with charcoal and then anhydrous magnesium surface (10 pounds). After filtration the solvents are removed in vacuo (40°, 3 Torr) to obtain a tan solid which is dried in vacuo (25°, 3 Torr) for 2 days to obtain 4-chloro-3,5-dimethylnitrobenzene, m.p. 101°–105°.

Powdered anhydrous potassium carbonate (1.95 kg, 14.1 mol) is suspended in anhydrous dimethyl sulfoxide (20 L) and to this suspension is added 4-benzyloxy-3-isopropyl-phenylacetate (2.36 kg, 9.74 mol) and 4-chloro-3,5-dimethylnitrobenzene (1.81 kg, 9.74 mol). This mixture is heated to an internal temperature of 12:5° for 23 hours. After cooling to 40° the reaction mixture is diluted with ice water (40 L). The precipitate is filtered, washed with water 5×4 L) and air-dried for 48 hours to obtain partially wet brown solids. The product is dissolved in hot isopropanol (4 L) and to this refluxing solution is added charcoal (KB, 200 g). After stirring at reflux for 0.5 hour, the mixture is filtered hot and the filtrate is cooled to 10° for 1 hour. The solids are collected by filtration and washed with cold (4°) isopropanol (3×500 mL). After drying overnight (25°, 3 Torr) the product is subjected to crystallization from isopropanol (3 L) to obtain 3,5-dimethyl-4-(3'-isopropyl-4'-benzyloxyphenoxy) -nitrobenzene, m.p. 99°–100°.

3,5-Dimethyl-4-(3'-isopropyl-4'-benzyloxyphenoxy)-nitrobenzene, (2.86 kg, 7.31 mol) is dissolved in a mixture of ethanol/tetrahydrofuran (10:1, 114L) and cooled to 10°. This is admixed with 10% Pd/C (800g) and the system is pressurized to 15 psi with hydrogen gas. The hydrogenation is continued for 18 hours. The mixture is then filtered through Celite and the Celite is washed with tetrahydrofuran (30 L). The filtrate is then evaporated in vacuo to dryness (50°, 3 Torr). The solid residue is triturated with heptane (3L) and filtered. The filter cake is washed with heptane (2×500 mL) to obtain crude product which is then dissolved in hot ethyl acetate (14 L) and diluted with heptane (30 L). The product slowly precipitates and the mixture is cooled at 10°for 1 hour, collected by filtration and washed with ethyl acetate/hexane 1:2 (2×500 mL). The filter cake is then dried (60°, 3 Torr) for 24 hours to yield 3,5-dimethyl4-(3'-isopropyl-4'-hydroxyphenoxy)-aniline, m.p. 180°–181°.

EXAMPLE 40

Ethyl N-[3,5-dimethyl-4-(4'-hydroxy-3'-isopropylphenoxy)-phenyl]oxamate (1.59 kg, 4.2 mol) is suspended in aqueous sodium hydroxide solution (1.0 N, 12 L) at room temperature (24°). After stirring at this temperature for 4 hours a bluish solution is obtained. This is filtered to remove some sediment and the filtrate is added slowly to a solution of hydrochloric acid (12 N, 1.4 L) in methanol (8 L), precipitating a solid. The slurry is stirred for 1 hour and the solids are collected by filtration, washed with water (4×500 mL) and dried overnight (60°, 2 Torr) to obtain crude acid, mp 185° dec. This is dissolved in ethyl acetate (6.5 L) at room temperature and to this solution is added charcoal (KB, 100 g). After stirring for 0.5 hour, the mixture is filtered and diluted with heptane (16.3L). After stirring at room temperature for 2 hours, the solids are collected by filtration, washed with ethyl acetate/heptane (1:2.5, 2×500 mL) and dried overnight (65°, 0.5 Torr) to yield product, m.p. 187°. This material is dissolved in hot acetonitrile (4 L) and to this is added HPLC grade water (12 L) slowly, keeping the temperature at 60° until the addition is complete. The solution is allowed to crystallize slowly at 50° and after initiation of the crystallization, cooling is slowly applied and then the mixture is kept at 10° for 1 hour. The product is collected by filtration, washed with acetonitrile/water (1:4, 2×500 mL) and dried invacuo (70°, 0.5 Torr) for 24 hours. The material is then sieved and redried for 48 hours (70°, 0.5 Torr) to obtain N-[3,5-dimethyl4-(4'-hydroxy-3'-isopropylphenoxy)-phenyl]oxamic acid, m.p. 187°-188°.

EXAMPLE 41

[5-(4-Amino-2,6-dimethylphenoxy)-2-hydroxyphenyl](4-fluorophenyl)methanone (48g. 0.13 mol) and diethyl oxalate (99.7 gm, 0.6 mol) are combined and heated with stirring under a nitrogen atmosphere at 100° for 10 hours. The reaction is stirred to room temperature overnight and the resulting suspension trimanted with heptane (300 ml). The product is filtered, washed with heptane (3×100 ml) and dried in vacuo at 60°/3 mmHg to give ethyl N-[4-[3'-(4-fluorobenzoyl)4'-hydroxyphenoxy]3,5-dimethylphenyl]oxamate, m.p. 150°-152°.

The starting material is prepared as follows:

A mixture of dimethylsulfoxide (875 ml), p-methoxyphenol (43.3g 0.3 48 mol), powdered potassium carbonate (69.9 g, 0.5 mol) and 4-chloro-3,5-dimethylnitrobenzene (see example 39, 64.6 g; 0.348 mol) is heated at a temperature of 125° for 18 hours. The suspension is cooled to 25° and pumped onto ice water (2620 ml) with stirring. The mixture is stirred for 2 hours, the product is filtered, washed with water (4×300 ml) and air dried. A solution of the product in tert-butylmethyl ether (3L) is dried over magnesium surface and treated with charcoal (6.4g) for 2.5 hours. The drying agent is filtered off and the filtrate concentrated in vacuo at 50°/3mm Hg to give product which is recrystallized from toluene (212ml) and petroleum ether (600 ml) to give 3,5-dimethyl-4-(4'-methoxyphenoxy)nitrobenzene, m.p. 120°-123°.

The above nitrobenzene derivative is then converted to (4-fluorophenyl)[2-hydroxy-5-(2,6-dimethyl-4-nitrophenoxy)phenoxy)phenyl]methanone similarly to procedures described in example 27.

(4-Fluorophenyl)[2-hydroxy-5-(2,6-dimethyl-4-nitrophenoxy)phenyl]methanone (62.8g, 0.16 mol) is dissolved in ethyl acetate (4L) and hydrogenated at atmospheric pressure over 5% platinum on carbon (13.2g). When the theoretical amount of hydrogen is consumed, the hydrogenation is stopped, the catalyst is filtered off, and the ethyl acetate solution is concentrated to dryness at 50°/3mm Hg. The residue is triturated hot with isopropanol (1L) and collected to yield [5-(4-amino-2,6-dimethylphenoxy)-2-hydroxyphenyl](4-fluorophenyl)methanone, m.p. 198°-202°.

EXAMPLE 42

To a stirred suspension of sodium borohydride (5.42g, 0.14 mol) in tetrahydrofuran (310 ml) at 0° under a nitrogen atmosphere is added acetic acid (17.3 gm, 0.29 mol) over 1 hour. The cooling bath is removed and the suspension is stirred at 24°. Ethyl N-[4-[3'-(4-fluorobenzoyl)-4'-hydroxyphenoxy]-3,5-dimethylphenyl]oxamate (60.3g, 0.13 mol) is added portionwise to the suspension over 5 minutes. The solution is stirred for 3 hours at 24°. The reaction is cooled to 10° and water (604 ml) is added. The pH is adjusted to 5-7 with a saturated sodium bicarbonate solution (180 ml). The product is extracted with ether (3×1L), washed with brine (1L), dried over sodium sulfate, filtered and concentrated at 50°/3 mm Hg to give crude product. A solution of the crude product in ethyl acetate (50 ml) is passed over a column of Kiesel gel 60 (23–400 mesh) using a mixture of ethyl acetate (7.5 L) and heptane (2.5 L) as the eluent.

The resulting product is dissolved in ethyl acetate (1.1 L), treated with charcoal (12 g), filtered and concentrated in vacuo to give a foam. The foam is dissolved in 470 ml of ethyl acetate and crystallized out with the addition of heptane (660 ml). The mixture is stirred for 48 hours and the product is filtered, washed with a mixture of heptane (20 ml) and ethyl acetate (10 ml) and dried in vacuo at 60°/3 mmHg to give ethyl N-[4-[3'-[(4-fluorophenyl) hydroxymethyl]-4'-hydroxyphenoxy]3,5-dimethylphenyl]oxamate, m.p. 148°-150°.

EXAMPLE 43

The following compounds are prepared using procedures similar to those described herein:

(a) ethyl N-[3,5-dichloro-4-[3'-[(4-chlorophenyl)hydroxymethyl]4'-hydroxyphenoxy]phenyl]oxamate;
(b) ethyl N-[4-[3'-[(4-chlorophenyl)hydroxymethyl]-4'-hydroxyphenoxy]-3,5-dimethylphenyl]oxamate;
(c) ethyl N4-[3'-(phenyl-hydroxymethyl)-4'-hydroxyphenoxy]-3,5-dimethylphenyl]oxamate;
(d) ethyl N-[4-[3'-[(4-tolyl)hydroxymethyl]-4'-hydroxyphenoxy]-3,5-dimethylphenyl]oxamate;
(e) ethyl N-[4-[3'-[(4-fluorophenyl)hydroxymethyl]4'-methoxyphenoxy]-3,5-dimethylphenyl]oxamate, m.p. 155°-156°.

EXAMPLE 44

Ethyl N-[4-[3'-[(4-fluorophenyl)hydroxymethyl]-4'-hydroxyphenoxy]-3,5-dimethylphenyl]oxamate according to Example 42 is resolved by high pressure liquid chromatography (HPLC) on a chiral OD (Daicel) column (cellulose para-methylbenzoate coated on silica gel) eluting with 80:20 hexanedethanol to give isomer A (retention time 115 minutes), $\alpha_D = +23.1°$ C. (c=0.64 in acetonitrile), m.p. 150°-152° C.; and isomer B (retention time 150 minutes), $\alpha_D = -21.7°$ C. (c=0.47 in acetonitrile), m.p. 147°-150° C.

EXAMPLE 45

Preparation of 10,000 tablets each containing 0.2 mg of the active ingredient, for example, N-[3,5-dimethyl-4-(4'-hydroxy-3'-isopropylphenoxy)-phenyl]oxamic acid,

| | |
|---|---|
| Active ingredient | 2.00 g |
| Lactose | 2,535.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 0.01–10 mg of one of the other compounds disclosed and exemplified herein.

EXAMPLE 46

Preparation of 1,000 capsules each containing 0.05 mg of the active ingredient, for example, ethyl N-[4-[3'-[(4-fluorophenyl) hydroxymethyl]-4'-hydroxyphenoxy]-3,5-dimethylphenyl]oxamate

| Active ingredient | 0.05 g |
|---|---|
| Lactose | 217.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 0.01–10 mg of the other compounds disclosed and exemplified herein.

What is claimed is:

1. A method of treating hypercholesterolemia in mammals which comprises administering to a mammal in need of such treatment an effective cholesterol-lowering amount of a compound of the formula

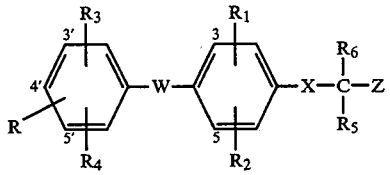
(I)

wherein
R is hydroxy, esterified hydroxy or etherified hydroxy;
$R_1$ is halogen, trifluoromethyl or lower alkyl;
$R_2$ is halogen, trifluoromethyl or lower alkyl;
$R_3$ is halogen, trifluoromethyl, lower alkyl, aryl, aryl-lower alkyl, cycloalkyl or cycloalkyl-lower alkyl; or
$R_3$ is the radical

wherein $R_8$ is hydrogen, lower alkyl, aryl, cycloalkyl, aryl-lower alkyl or cycloalkyl-lower alkyl; $R_9$ is hydroxy or acyloxy; $R_{10}$ represents hydrogen or lower alkyl; or $R_9$ and $R_{10}$ together represent oxo;

$R_4$ is hydrogen, halogen, trifluoromethyl or lower alkyl;
X is $-NR_7$;
W is O or S;
$R_5$ and $R_6$ together represent oxo;
$R_7$ represents hydrogen or lower alkyl;
Z represents carboxyl, carboxyl derivatized as a pharmaceutically acceptable ester or as a pharmaceutically acceptable amide; and aryl in any of the above definitions represents carbocyclic aryl; or a pharmaceutically acceptable salt thereof.

2. A method according to claim 1 which comprises administering a compound of formula I wherein R is located at the 4'-position, $R_1$ and $R_2$ are located at the 3 and 5 positions, and $R_3$ and $R_4$ are located at the 3' and 5'-positions; or a pharmaceutically acceptable salt thereof.

3. A method according to claim 1 which comprises administering a compound of formula I wherein X and W represent O.

4. A method according to claim 1 which comprises administering a compound of the formula

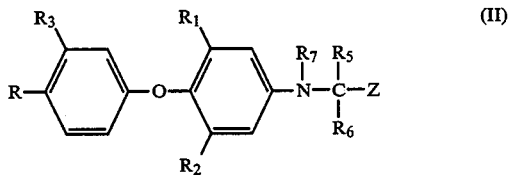
(II)

wherein R is hydroxy, esterified hydroxy or etherified hydroxy; $R_1$ and $R_2$ independently represent halogen, trifluoromethyl or $C_1-C_3$alkyl; $R_3$ represents lower alkyl, lower alkanoyl, hydroxy-lower alkyl, carbocyclic arylmethyl, carbocyclic aroyl or carbocyclic arylhydroxymethyl; $R_5$ and $R_6$ together represent oxo; $R_7$ represents hydrogen or lower alkyl; and Z represents carboxyl or carboxyl derivatized in form of a pharmaceutically acceptable ester or amide; or a pharmaceutically acceptable salt thereof.

5. A method of treating hypercholesterolemia in mammals which comprises administering to a mammal in need of such treatment an effective cholesterol-lowering amount of a compound of the formula

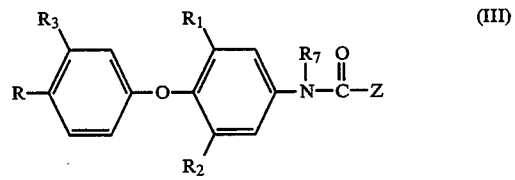
(III)

wherein R is hydroxy, esterified hydroxy or etherified hydroxy; $R_1$ represents halogen, trifluoromethyl or $C_1-C_3$alkyl; $R_2$ represents halogen, trifluoromethyl or $C_1-C_3$alkyl; $R_3$ represents lower alkyl, carbocyclic aroyl, carbocyclic arylmethyl or carbocyclic arylhydroxymethyl; $R_7$ represents hydrogen or lower alkyl; Z represents carboxyl or carboxyl derivatized as a pharmaceutically acceptable ester or amide; or a pharmaceutically acceptable salt thereof.

6. A method according to claim 5 which comprises administering a compound of formula III wherein R represents hydroxy, acyloxy, lower alkoxy or tetrahydropyranyloxy; or of a pharmaceutically acceptable salt thereof.

7. A method according to claim 5 which comprises administering a compound of formula III wherein R is hydroxy, lower alkanoyloxy, lower alkoxy or tetrahydropyranyloxy; $R_1$ and $R_2$ represent halo or $C_1$-$C_3$-alkyl; $R_3$ is $C_1$-$C_3$-alkyl or monocyclic carbocyclic arylmethyl; $R_7$ is hydrogen or $C_1$-$C_2$-alkyl; Z is carboxyl or carboxyl derivatized as a pharmaceutically acceptable ester or amide; or a pharmaceutically acceptable salt thereof.

8. A method according to claim 5 which comprises administering a compound of formula III wherein Z is carboxyl or carboxyl esterified as a pharmaceutically acceptable ester; or a pharmaceutically acceptable salt thereof.

9. A method according to claim 5 which comprises administering a compound of formula III wherein $R_1$ and $R_2$ represent chloro or methyl; $R_3$ is isopropyl, benzyl or benzyl substituted by halogen, lower alkyl, lower alkoxy or trifluoromethyl; $R_7$ is hydrogen; Z is carboxyl or lower alkoxycarbonyl; or a pharmaceutically acceptable salt thereof.

10. A method according to claim 9 which comprises administering N-[3,5-dimethyl-4-(4'-hydroxy-3'-isopropylphenoxy)-phenyl]-oxamic acid or a pharmaceutically acceptable salt thereof.

11. A method according to claim 9 which comprises administering N-[3,5-dichloro-4-(4'-hydroxy-3'-isopropylphenoxy)-phenyl]-oxamic acid or a pharmaceutically acceptable salt thereof.

12. A method according to claim 5 which comprises administering a compound of formula III wherein R is hydroxy, lower alkanoyloxy, lower alkoxy or tetrahydropyranyloxy; $R_1$ and $R_2$ represent halo or $C_1$-$C_3$-alkyl; $R_3$ is carbocyclic aroyl or carbocyclic arylhydroxymethyl; $R_7$ is hydrogen or $C_1$-$C_2$-alkyl; Z is carboxyl or carboxyl derivatized as a pharmaceutically acceptable ester or amide; or a pharmaceutically acceptable salt thereof.

13. A method according to claim 5 which comprises administering a compound of formula III wherein R is hydroxy; $R_1$ and $R_2$ represent chloro or methyl; $R_3$ is phenyl-hydroxymethyl or phenyl-hydroxymethyl substituted on phenyl by halogen, lower alkyl, lower alkoxy or trifluoromethyl; or $R_3$ is benzoyl or benzoyl substituted by halogen, lower alkyl, lower alkoxy or trifluoromethyl; $R_7$ is hydrogen; Z is carboxyl or lower alkoxycarbonyl; or a pharmaceutically acceptable salt thereof.

14. A method according to claim 13 which comprises administering ethyl N-[4-[3'-[(4-fluorophenyl)hydroxymethyl]-4'-hydroxyphenoxy]-3,5-dimethylphenyl]oxamate or an enantiomer thereof.

15. A method according to claim 13 which comprises administering N-[4-[3'-[(4-fluorophenyl)hydroxymethyl]-4'-hydroxyphenoxy]-3,5-dimethylphenyl]oxamic acid, an enantiomer thereof or a pharmaceutically acceptable salt thereof.

* * * * *

UNITED STATES PATENT AND TRADEMARK OFFICE
CERTIFICATE OF CORRECTION

PATENT NO. : 5,401,772
DATED : March 28, 1995
INVENTOR(S) : Naokata Yokoyama, Gordon N. Walker and Alan J. Main It is certified that error appears in the above-identified patent and that said Letters Patent is hereby corrected as shown below:

Column 36, Claim 3, lines 18-20, should read:

3. A method according to claim 1 which comprises administering a compound of formula I wherein W represents O.

Signed and Sealed this

Eleventh Day of June, 1996

Attest:

BRUCE LEHMAN

Attesting Officer

Commissioner of Patents and Trademarks